(12) United States Patent
Mutharasan et al.

(10) Patent No.: US 7,935,191 B2
(45) Date of Patent: May 3, 2011

(54) CONTROLLING ACCUMULATION OF SELECT ADSORBERS ON A PIEZOELECTRIC CANTILEVER SENSOR

(75) Inventors: Rajakkannu Mutharasan, West Chester, PA (US); David R. Maraldo, Gilbertsville, PA (US); Kishan Rijal, Harleysville, PA (US); Gossett Augustus Campbell, Conshohocken, PA (US)

(73) Assignee: Drexel University, Philadelphia, PA (US)

( * ) Notice: Subject to any disclaimer, the term of this patent is extended or adjusted under 35 U.S.C. 154(b) by 781 days.

(21) Appl. No.: 11/836,742

(22) Filed: Aug. 9, 2007

(65) Prior Publication Data

US 2008/0035180 A1   Feb. 14, 2008

Related U.S. Application Data

(60) Provisional application No. 60/821,883, filed on Aug. 9, 2006.

(51) Int. Cl.
 *B08B 7/02* (2006.01)
 *G01N 15/06* (2006.01)
 *G01N 29/00* (2006.01)
 *G01N 33/53* (2006.01)
 *G01N 33/48* (2006.01)
 *C12Q 1/00* (2006.01)

(52) U.S. Cl. ........ 134/1; 134/32; 134/42; 310/311; 73/61.75; 73/579; 435/4; 435/7.1; 435/287.2; 436/149; 436/518; 436/524; 436/525; 422/68.1; 422/82.01

(58) Field of Classification Search .................. None
See application file for complete search history.

(56) References Cited

U.S. PATENT DOCUMENTS

| 3,560,099 | A |   | 2/1971  | Boes et al. |
| 4,186,599 | A |   | 2/1980  | Frick |
| 4,791,818 | A |   | 12/1988 | Wilde et al. |
| 5,116,759 | A |   | 5/1992  | Klainer et al. |
| 5,583,300 | A |   | 12/1996 | Green et al. |
| 5,719,324 | A | * | 2/1998  | Thundat et al. ............ 73/24.01 |
| 5,770,462 | A |   | 6/1998  | Molloy |
| 6,170,981 | B1 |  | 1/2001  | Regnier et al. |
| 6,336,366 | B1 |  | 1/2002  | Thundat et al. ........... 73/514.34 |

(Continued)

FOREIGN PATENT DOCUMENTS

WO    WO 2005043126 A2 *  5/2005

OTHER PUBLICATIONS

U.S. Appl. No. 11/659,919, filed Jan. 23, 2007, Mutharasan, et al.

(Continued)

*Primary Examiner* — Michael Kornakov
*Assistant Examiner* — Nicole Blan
(74) *Attorney, Agent, or Firm* — Woodcock Washburn, LLP

(57) ABSTRACT

The techniques described herein are directed to removing material that has attached to or preventing material from attaching to the surface of a piezoelectric cantilever. The material can be a target material, other, non-target, material that may be weakly bound or attached to the cantilever sensor, or the material may be a combination thereof. Accordingly, the cantilever sensor can be reused, in situ, without degraded detection performance of the cantilever sensor. The techniques may also be utilized to remove all material that has attached to a surface of the cantilever sensor which provides means for reusing the cantilever sensor.

32 Claims, 15 Drawing Sheets

U.S. PATENT DOCUMENTS

| | | | |
|---|---|---|---|
| 6,543,274 | B1 | 4/2003 | Herrmann et al. |
| 6,880,402 | B1* | 4/2005 | Couet et al. ............... 73/579 |
| 7,105,301 | B2 | 9/2006 | Su et al. |
| 7,409,851 | B2 | 8/2008 | Llic et al. |
| 7,458,265 | B2* | 12/2008 | Shih et al. ............... 73/579 |
| 7,504,219 | B2 | 3/2009 | Bickmore, Jr. et al. |
| 2002/0092340 | A1 | 7/2002 | Prater et al. |
| 2003/0215816 | A1 | 11/2003 | Sundararrajan et al. |
| 2005/0112621 | A1 | 5/2005 | Kim et al. |
| 2008/0034840 | A1 | 2/2008 | Mutharasan et al. |
| 2008/0035180 | A1 | 2/2008 | Mutharasan et al. |

OTHER PUBLICATIONS

U.S. Appl. No. 11/747,183, filed May 10, 2007, Mutharasan, et al.
U.S. Appl. No. 60/746,951, filed May 10, 2006, Mutharasan, et al.
U.S. Appl. No. 60/761,172, filed Jan. 23, 2006, Mutharasan, et al.
U.S. Appl. No. 60/807,020, filed Jul. 11, 2006, Mutharasan, et al.
Campbell, G.A., et al., "Detection of *Bacillus anthracts* spores and a model protein using PEMC sensors in a flow cell at 1 mL/MIN," Biosensors and Bioelectronics, 1-29, 2005.
Campbell, G.A., et al., "A method of measuring *Escherichia coli* 0157:h7 AT 1 CELL/M1 IN 1 liter sample using antibody functionalized piezoelectric-excited millimeter-sized cantilever," Environmental Science & Technology, 1-23, 2006.
Campbell, G., et al., "Detection of airborne *Bacillus anthracis* spores by an integrated system of an air sample and a cantilever immunosensor," Sensors and Actuators B, 1-25, 2006.
Campbell, G.A., et al., "PEMC sensor's mass change sensitivity in 20 PG/HZ under liquid immersion," Biosensors and Bioelectronics, 1-28, 2005.
Campbell, G.A., et al., "Piezoelectric-excited millimeter-sized cantilever (PEMC) sensors measure albumin interaction with self-assembled monolayers of alkanethiols having different functional head groups," J of Analytical Chem., 1-27, 2005.
Campbell, G.A., et al., "Detection and quantification of proteins using self-excited PZT-glass millimeter-sized cantilever," Biosensors and Bioelectronics, 26-36, 2005.
Campbell, G.A., "Piezoelectric-excited millimeter-sized cantilever (PEMC) sensors detect *Bacillus anthracis* at 300 spores/mL," Biosensors and Bioelectronics, 37-45, 2005.
Campbell, G.A., et al., "Kinetics of *Bacillus anthracis* spore binding to antibody functionalized PEMC sensors in presence of *Bacillus thuringiensis* and *Bacillus cereus*," J. Publications, Am. Chem. Soc., 25 pages, 2006.
Campbell, G.A., et al., "*Escherichia coli* O157:H7 detection limit of millimeter-sized PZT cantilever sensors in 700 cells/mL," Analytical Sci., 11-13, 2005.
Campbell, G.A., et al., "Detection of pathogen *Escherichia coli* O157:H7 using self-excited PZT-glass microcantilevers," Biosensors and Bioelectronics, 14-25, 2004.
Campbell, G.A., "Detection of staphylococcus enterotoxin B at pictogram levels using piezoelectric-excited millimeter-sized cantilever sensors," Submitted on-line to J. of Analytical Chem, 1-24, 2006.
Campbell, G.A., et al., "Detect of *Escherichia coli* O157:H7 in ground beef samples using piezoelectric excited millimeter-sized cantilever (PEMC) sensors," Biosensors and Bioelectronics, 2006, 1-7, 2006.
Carr, D.W., et al., "Fabrication of nanoelectromechanical systems in single crystal silicon using silicon on insulator substrates and electron beam lithography," J. Vac. Sci. Technology, B, 5(6), 2760-2763, 1997.
Maraldo, D., et al., "10-minute assay for detecting *Escherichia coli* O157:H7 in ground beef samples using piezoelectric-excited millimeter-sized cantilever (PEMC) sensors," J. of Food Protection, 1-31, 2007.
Wilson, L., et al., "Viscosity and density values from excitation level response of piezoelectric-excited cantilever sensors," Sensors and Actuators A, 2007, 138, 44-51, 2007.
Campbell et al., Sensing of Liquid level at Micron Resolution using Self-Excited millimeter-sized sized PZT-cantilever, Sensors and Actuators A, May 25, 2005, 122, 326-334.

* cited by examiner

CONTROLLING ACCUMULATION OF SELECT ADSORBERS ON A PIEZOELECTRIC CANTILEVER SENSOR

CROSS-REFERENCE TO RELATED APPLICATIONS

This application claims priority from Provisional U.S. Patent Application No. 60/821,883, entitled FLOW CELLS FOR PIEZOELECTRIC CANTILEVER SENSORS, filed Aug. 9, 2006, the contents of which are hereby incorporated by reference in its entirety. This application also claims priority from Provisional U.S. Patent Application No. 60/940,861, entitled SELF-EXCITING, SELF-SENSING PIEZOELECTRIC CANTILEVER SENSOR, filed May 30, 2007, the contents of which are hereby incorporated by reference in its entirety. This application also claims priority from Provisional U.S. Patent Application No. 60/948,106, entitled DETECTION OF DNA STRANDS IN BUFFER AND COMPLEX MEDIA THROUGH DIRECT HYBRIDIZATION AND BY EXTENSION USING POLYMERASE, filed Jul. 5, 2007, the contents of which are hereby incorporated by reference in its entirety. This application is related to U.S. patent application Ser. No. 11/625,919, entitled "SELF-EXCITING, SELF-SENSING PIEZOELECTRIC CANTILEVER SENSOR," filed Jan. 23, 2007, which is hereby incorporated by reference in its entirety.

TECHNICAL FIELD

The technical field generally relates to cantilever sensors and more particularly relates to removing material from a cantilever sensor and/or preventing material from accumulating on a cantilever sensor.

BACKGROUND

A known technique for detecting a target material, such as a protein of a pathogen, for example, involves placing a cantilever sensor in a medium for a period of time. The cantilever sensor is designed such that target material present in the medium will bind or attach to the cantilever sensor. Typically, after use, the sensor is discarded or cleaned for reuse. Discarding cantilever sensors can be expensive and an inefficient use of resources. Attempts have been made to clean a sensor after use. Typically, cleaning a sensor involves a chemical rinse or the like. Use of chemical rinses to clean cantilever sensors can be a time consuming processing. Further, chemical rinses are known to damage the cantilever sensor and degrade detection performance of the cantilever sensor.

SUMMARY

Material is removed from a cantilever sensor and/or prevented from accumulating on a cantilever sensor via the application of mechanical energy to either the cantilever sensor or the medium in which the cantilever sensor is placed, or both. The removal/prevention technique is nondestructive to the cantilever sensor. In an example embodiment, a millimeter-sized piezoelectric cantilever sensor is utilized. The techniques described herein are directed to removing material that has attached to a piezoelectric cantilever sensor surface and to preventing material from attaching to a surface of a piezoelectric cantilever. The material can be the target material, the material can be other, non-target, material that may be weakly bound or attached to the cantilever sensor, or a combination thereof. Accordingly, the cantilever sensor can be reused, in situ, without degraded detection performance of the cantilever sensor.

In an example embodiment, non-target weak adsorbers are selected for removal from the piezoelectric cantilever sensor via various techniques. In a first technique, the source of the mechanical energy is an electrical signal that is applied to remove weak adsorbers. In a second technique, the source of the mechanical energy is ultrasound that is applied to remove weak adsorbers. In a third technique, the movement of flow of the medium (e.g., fluid: liquid or gas vacuum) in which the piezoelectric cantilever sensor is placed is disturbed or modified (e.g. change the flow rate or local velocity of the medium proximate to the sensor) to remove weak adsorbers. In essence, as a result of these techniques, material is shaken off of a surface of the cantilever sensor. These techniques are applicable, in situ, while the detection process of target material is being conducted.

In another example embodiment, these techniques can be used to prevent accumulation of material on the cantilever sensor, in situ, during the detection process. The removal and prevention techniques may be utilized in combination or separately. For example, if utilized, in situ, any of the techniques may be used to prevent material from accumulation on the surface and the same or a different technique may be used to remove non-target material that has weakly attached to the surface. The application of these techniques, by removing non-target material and/or preventing the accumulation of non-target material on the cantilever sensor, provides means for an extremely accurate measurement of accumulated target material.

In another example embodiment, these techniques are utilized to remove all material (e.g., target material and non-target material) that has attached to a surface of the cantilever sensor. The adsorbers selected for removal in this example embodiment include all material that has attached to the sensor. This technique provides means for reusing the cantilever sensor.

Exposure of the piezoelectric cantilever sensor to a medium may be done for the purpose of detecting/measuring a target material in a medium. The removal and prevention techniques can be utilized to eliminate at least a portion of the added mass of non-targeted material, which can result in a more accurate measurement of the target material that is in the medium. Even removing only a portion of the weak adsorbers by this method will open up available sites for the target material, thereby improving the options for detecting/measuring accumulated target material.

DETAILED DESCRIPTION OF ILLUSTRATIVE EMBODIMENTS

Figure 1:
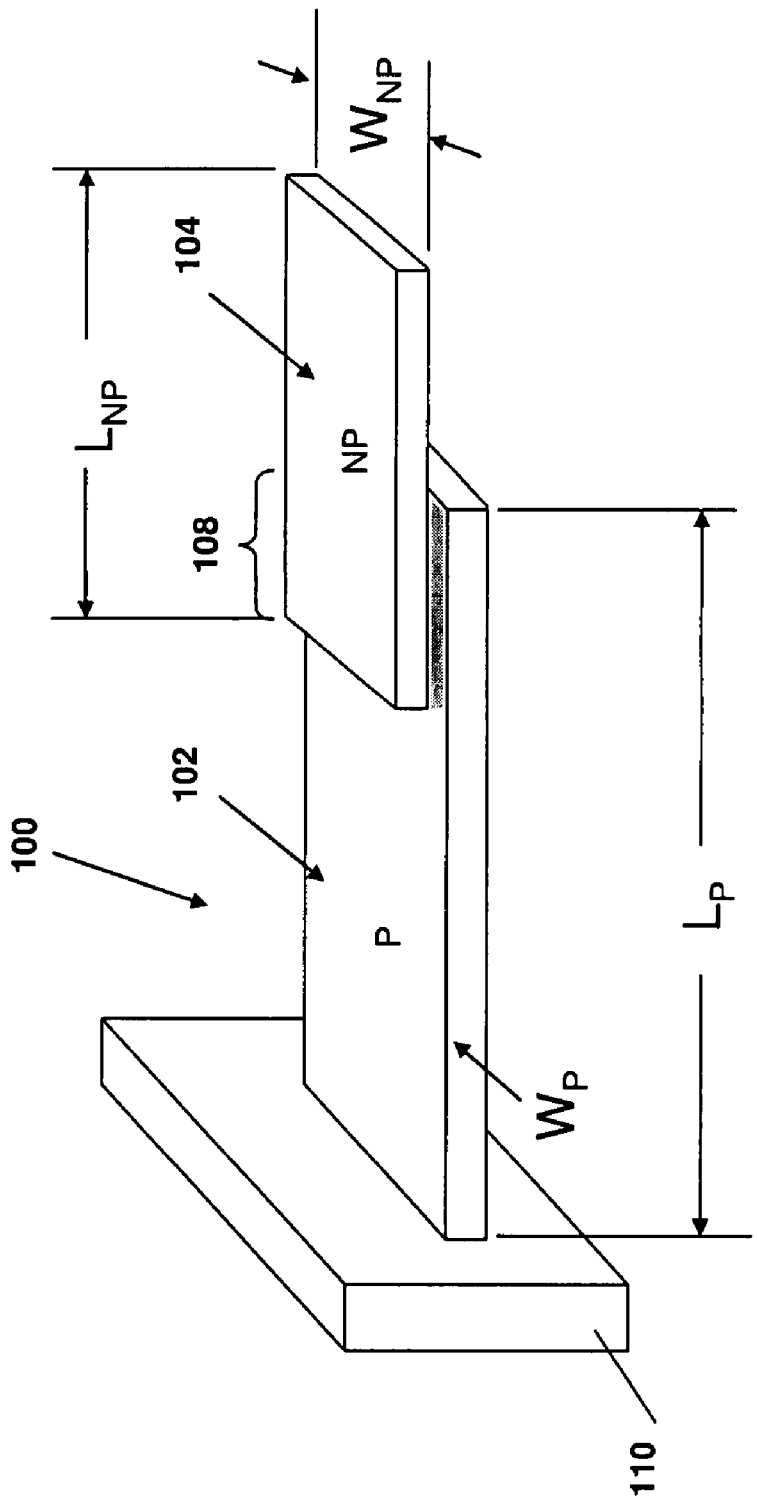
FIG. 1 is an illustration of an example configuration of a self-exciting, self-sensing piezoelectric cantilever sensor.

Targeted or non-targeted material may be directly or indirectly bound to the surface of a sensor, such as the non-piezoelectric surface of a piezoelectric cantilever sensor. The techniques described herein relate to methods of removing material that has accumulated and/or preventing material from accumulating on the surface of a sensor. The techniques described herein are as applied to a piezoelectric cantilever sensor. However, application is not limited thereto. The herein described techniques are applicable to other than piezoelectric sensors. It is noted that the techniques described may be used to remove all of the material accumulated on a sensor, remove a portion of the material whether it be targeted or non-targeted material, or prevent accumulation.

"Material", as used herein, refers to anything that attaches or bonds to the sensor surface, including non-targeted material, molecules, analyte, adsorbers, etc. "Sensor surface", "surface", and similar terminology is used generally to refer to the surface of a sensor, such as the surface of a piezoelectric cantilever sensor, including any coating or other type of layer that may be on the surface, such as a bonding agent. The mechanical methods are described herein as causing a vibration, a stimulation, or motion of the sensor or the medium. However, the result of the mechanical methods are not limited to these results and include any similar result such as a pulsation, oscillation, vacillation, or the like, to the sensor or sample medium.

As shown by example embodiments of the techniques described, the application of mechanical or vibrational energy to the sensor may be used to cause the attachment of certain material(s) in the medium to the bonding agent to weaken and release. The removal of all of the bound molecules in this manner enables the re-use of the cantilever sensor without degrading the sensor, the bonding agent, or the sample material.

It may also be desired to remove only a portion of, or weaken the bonds of, only a portion of the material that has attached to a sensor. For example, when exposing a piezoelectric cantilever sensor to a medium that contains both targeted material and non-targeted material, the bonding agent may not only bond to the target material but may also cause a weak bond with non-target weak adsorbers. Also, the piezoelectric cantilever sensor may have material that accumulated on the piezoelectric cantilever sensor prior to exposure to this particular medium. Since the sensor has a fixed binding area, the available sites decrease as material accumulates on the surface of the piezoelectric cantilever sensor when exposed to the sample medium. If non-target material attaches to the sensor surface, then there are less available sites for the target material. Also, when measuring a target material in a medium, the added mass of the non-targeted material can result in an inaccurate mass measurement of the target material that is in the sample. Since the attachment of the non-targeted weak material to the bonding agent is typically a weak attachment, a lesser applied mechanical stimulation can achieve the result of releasing these weak adsorbers without weakening the attachment of the target analyte. Even removing only a portion of the weak adsorbers by this method opens up available sites for the target material, thereby improving the options for measuring accumulated mass of the target material.

Some material will not attach to a sensor that has any or a low vibration. Similarly, some material will not attach when there is a sufficient disturbance to the medium in which the sensor is placed. Again, preventing non-targeted material from attaching to the sensor surface keeps available sites for the target material open.

The specific techniques of removal and prevention described below are examples of ways to cause vibration to a sensor or cause a disturbance in the medium to produce the desired results. The use of mechanical means to cause mechanical motion is described in the examples below in relation to a liquid. It is noted that the technique also can be utilized in other various mediums, such as a gas or vacuum.

A self-exciting, self-sensing piezoelectric cantilever sensor may be used with the techniques described. A piezoelectric cantilever sensor provides the ability to detect and measure extremely small amounts of a target material immersed in a liquid or contained in a gas or vacuum. Other sensors may be used to detect material in a medium and may also be used with the techniques described.

The detection of biological materials on a piezoelectric cantilever sensor first involves the immobilization of a recognition molecule such as an antibody or a receptor on the sensor surface. For example, antibody or DNA receptors may be immobilized on the surface of the sensor to bind target protein or DNA material. When the piezoelectric cantilever sensor is exposed to the medium, material can be directly or indirectly bound to the surface of the non-piezoelectric portion of the self-exciting, self-sensing piezoelectric cantilever sensor. Optionally, the sensor surface may be prepared with a coating, such as gold or an amine acid, for example, before immobilization of the recognition molecule. Coating the surface may aid in preventing non-specific adsorption.

To detect/measure the mass of the target material on the sensing apparatus, the resonance frequency of the piezoelectric cantilever sensor is measured. The measured resonance frequency is compared with a baseline resonance frequency to determine a difference in frequency. The difference in frequency is indicative of a mass of a material on the sensing apparatus. The difference is utilizable to detect accumulation of material on the sensor and/or to measure an amount of mass of material accumulated on the sensor. The ability of the piezoelectric cantilever sensor to measure the mass of the material that has accumulated on the sensor is referred to as the sensor's detection performance.

A self-exciting and self-sensing piezoelectric cantilever sensing apparatus includes a piezoelectric layer and a non-piezoelectric layer attached to the piezoelectric layer such that a distal end of the non-piezoelectric layer extends beyond a distal end of the piezoelectric layer or a distal end of the piezoelectric layer extends beyond a distal end of the non-piezoelectric layer. That is, the piezoelectric layer is coupled to the non-piezoelectric layer such that the piezoelectric layer and the non-piezoelectric layer are not coextensive FIG. 1 is an illustration of an exemplary self-exciting, self-sensing piezoelectric cantilever sensor that can be used with the removal and prevention techniques described herein. Piezoelectric cantilever sensor 100 comprises a piezoelectric portion 102 and a non-piezoelectric portion 104. Piezoelectric portions are labeled with an uppercase letter p ("P"), and non-piezoelectric portions are labeled with the uppercase letters np ("NP"). The piezoelectric portion 102 is coupled to the non-piezoelectric portion. The piezoelectric portion 102 and the non-piezoelectric portion overlap at region 108. The piezoelectric portion 102 is coupled to a base portion 110.

The width (e.g., $W_P$ in FIG. 1) of the piezoelectric portion (e.g., piezoelectric portion 102), and the width (e.g., $W_{NP}$ in FIG. 1) of the non-piezoelectric portion (e.g., non-piezoelectric portion 104), may be of variable widths. For example, when using an exemplary millimeter size piezoelectric cantilever sensor, the widths $W_P$ and $W_{NP}$ can range from about 0.1 mm to about 4.0 mm. The length (e.g., $L_P$ in FIG. 1) of the piezoelectric portion (e.g., piezoelectric portion 102), and the length (e.g., $L_{NP}$ in FIG. 1) of the non-piezoelectric portion (e.g., non-piezoelectric portion 104) may be of variable lengths. For example, when using the exemplary millimeter size piezoelectric cantilever sensor, the lengths $L_P$ and $L_{NP}$ can range from about 0.1 mm to about 10.0 mm. The mass change sensitivities of a millimeter size piezoelectric cantilever sensor to the sub-femtogram level make millimeter size piezoelectric cantilever sensors useful for higher order mass measurements.

Figure 2:
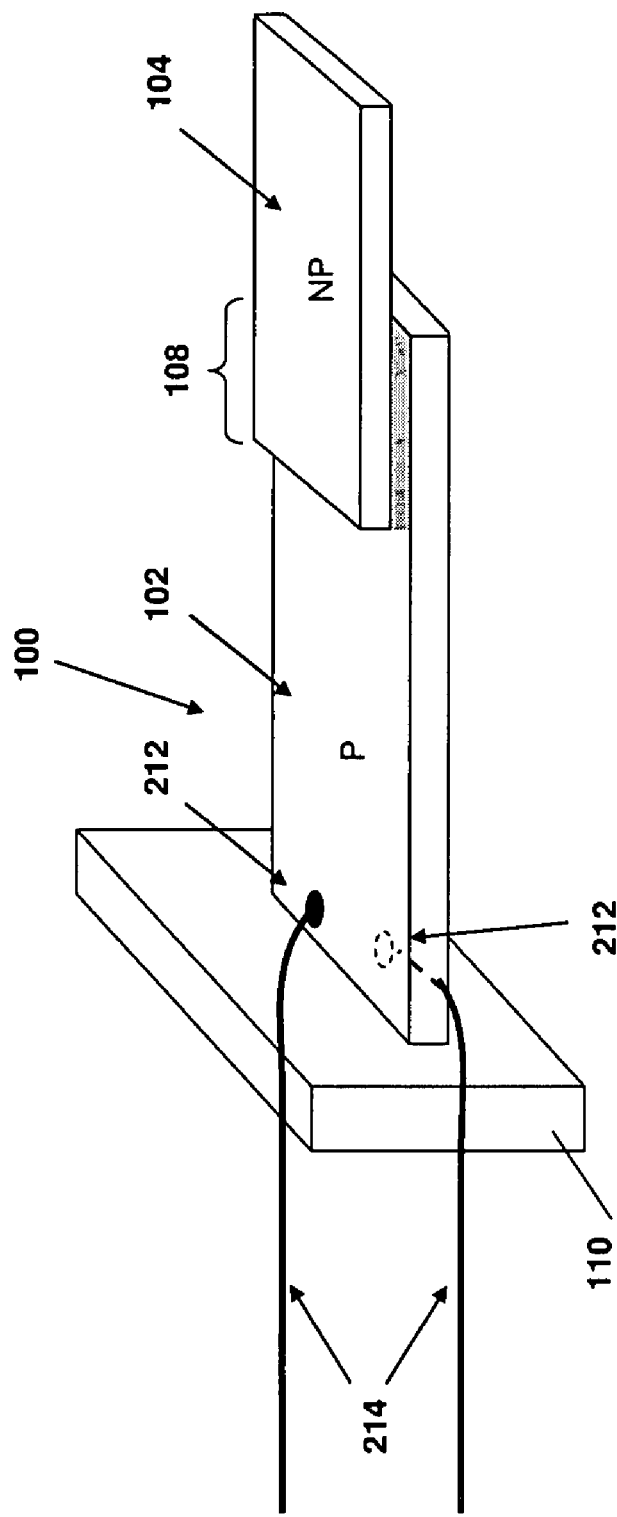
FIG. 2 is an illustration of an example configuration of a self-exciting, self-sensing piezoelectric cantilever sensor with electrodes attached.

FIG. 2 illustrates an example embodiment of the piezoelectric cantilever sensor configured with electrodes. The two surfaces of piezoelectric layer 102 are connected to a suitable measuring device. The connection shown in FIG. 2 is accomplished via electrical wires 214 attached to electrodes 212 and the electrodes may be utilized to provide an electrical signal to and receive an electrical signal from the piezoelectric portion. Any appropriate means (e.g., inductive means, wireless means) may provide the electrical signal. The signals can be analyzed by the measuring to determine the resonance frequency of the piezoelectric cantilever sensor. Electrodes, for example, may be placed at any appropriate location on a sensor. In an example embodiment, FIG. 2 depicts electrodes 214 as operatively located near a location of concentrated stress 212 in the piezoelectric layer 102. They can also be coupled to the piezoelectric portion 102 at any location not within the base portion 110 and not overlapped by the non-piezoelectric portion 104. Electrodes need not be placed symmetrically about the piezoelectric portion 102.

The herein described control techniques (techniques utilized to remove material accumulated on the sensor, techniques utilized to prevent accumulation of material on the sensor, or a combination thereof) are applicable to various types of sensors. For example, the herein described control techniques are applicable to piezoelectric sensors, cantilever sensors, and non-piezoelectric sensors. Further, the herein described control techniques are applicable to sensors of any appropriate size and dimensions. The techniques described herein may be employed similarly with these sensors to improve the accuracy of these measurements by removing non-target material from the sensor surface or preventing non-target material from binding altogether. In addition, the techniques described herein may be employed to remove, or "shake off", both target and non-target material so that the sensor may be re-used.

Figure 3:
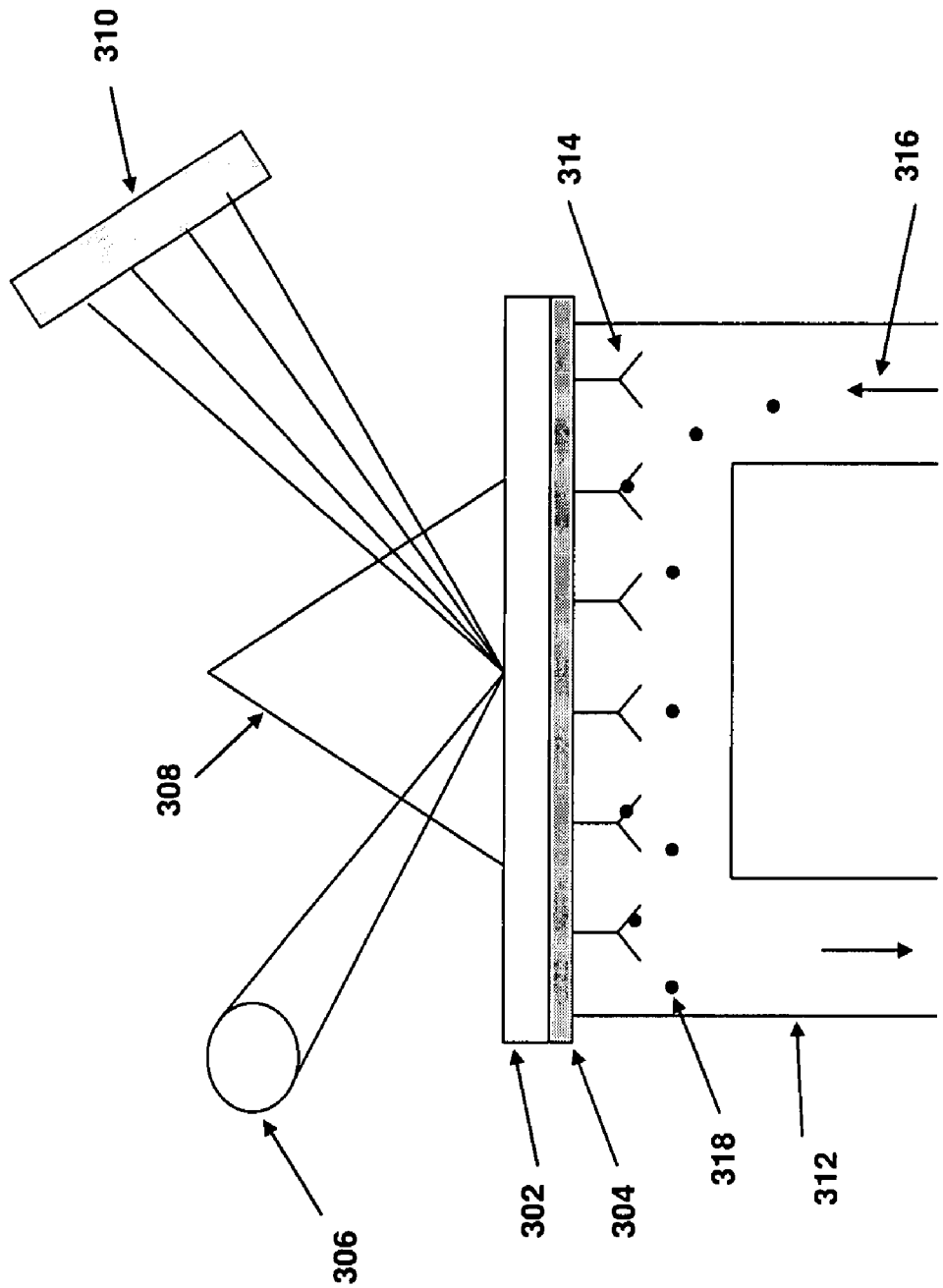
FIG. 3 is an illustration of an example configuration of a surface plasmon resonance (SPR) based sensor configured with an exemplary flow cell.

An example sensor that may be used with the techniques described herein is a surface plasmon resonance (SPR) based sensor 302, shown in FIG. 3. An SPR-based sensor 302 is able to detect an accumulated mass based on the sensor's response to a refractive index near the sensor surface. FIG. 3 illustrates a typical set up for surface plasmon resonance (SPR). The prism 308 serves to refract or reflect the light source 306 at the interface 304, where target material is detected. At the interface 304 of the flow cell 312 that is adjacent to the prism 308, antibody 314 is immobilized. The surface of the sensor 302 is positioned in relation to a flow cell, exposing the sensor to a medium with a flow rate, where the direction of flow is indicated by 316. Typically, a low flow rate is used (e.g. 100 microliters/minute). When material binds to the surface of a SPR sensor 302, changes in the refractive index of the medium may be measured for mass detection by an appropriate detector 310. If the surface of the sensor 302 that is immobilized with antibody is vibrated by any of the techniques discussed herein, non-specific adsorption can be reduced. Vibration and a modified flow rate may be combined to remove material that has attached to the surface and prevent material from attaching to the sensor surface.

Another well-known technique used to detect the presence of a target material in a medium is the Enzyme-Linked Immuno-Sorbent Assay (ELISA) assay. The removal and prevention techniques described herein may also be utilized to improve the detection of the ELISA technique. Similar to the piezoelectric cantilever sensor described above, performing an ELISA involves immobilizing a recognition molecule (e.g. antibody) on the surface of a solid support (e.g. polystyrene microtiter plate). After the recognition molecule is immobilized, the solid support is exposed to a medium. The recognition molecule may link to an enzyme, or target material, in the medium which is converted by the enzyme to elicit a chromogenic or flourogenic signal. The results can be viewed using a spectrophotometer or similar optical device.

During exposure of the sensor to the medium in the ELISA technique, flow and vibration to the surface has shown to reduce non-specific surface adsorption. The removal or prevention of non-specific surface adsorption improves the measurement of the target material that has adsorbed to the sensor surface. After the target material has attached to the surface, a second antibody may be introduced that attaches only to the target (that is attached to the sensor surface). A third antibody is contacted so that a signal proportional to the target material is generated. If the sensor surface, that has the antibody immobilized, is vibrated or has mechanical energy injected, non-specific adsorption may be reduced, similar to the phenomena observed with the piezoelectric cantilever sensor.

The removal and prevention techniques may be used to aid in DNA microarrays. A DNA microarray is a microscopic spot containing identical single-stranded molecules of deoxyribonucleotides (DNAs) that may be attached to a solid support. Microarrays utilize the hybridization process to measure gene expressions. Therefore, employing the removal and/or prevention techniques described herein may improve the hybridization of DNA. If two strands or pieces of DNA bind to one another (hybridize) then they are opposite strands of a single gene. Removal and/or prevention techniques may prevent weak material from attaching to the strands. Hybridization is not compromised by the vibration of the sensor or by modifying the flow rate of the medium.

Other example applications of a sensor, such as the piezoelectric cantilever sensor, and the removal/prevention techniques include the detection of bioterrorism agents, such as Bacillus anthracis, the detection of food-borne pathogens, such as E. coli, the detection of pathogens in food and water, the detection of certain cell types in body fluids (e.g., circulating tumor cells), the detection of biomarkers in body fluids (e.g., proteins that mark specific pathophysiology—alpha-fetoprotein, beta-2-microglobulin, bladder tumore antigen, breast cancer marker CA-15-3, and other CAs (cancer antigens), calcitonin, carcinoembryonic antigen, and others), the detection of markers of explosives such as trinitrotoluene, the presence of dinitrotoluene, and the detection of airborne and waterborne toxins. The self-exciting, self-sensing piezoelectric cantilever sensor also can be used for the detection of biological entities at pictogram levels, and for the detection of protein-protein interactions, both steady and kinetic.

Some specific examples of these and other applications are discussed in the Experimental Section below.

Figure 4:
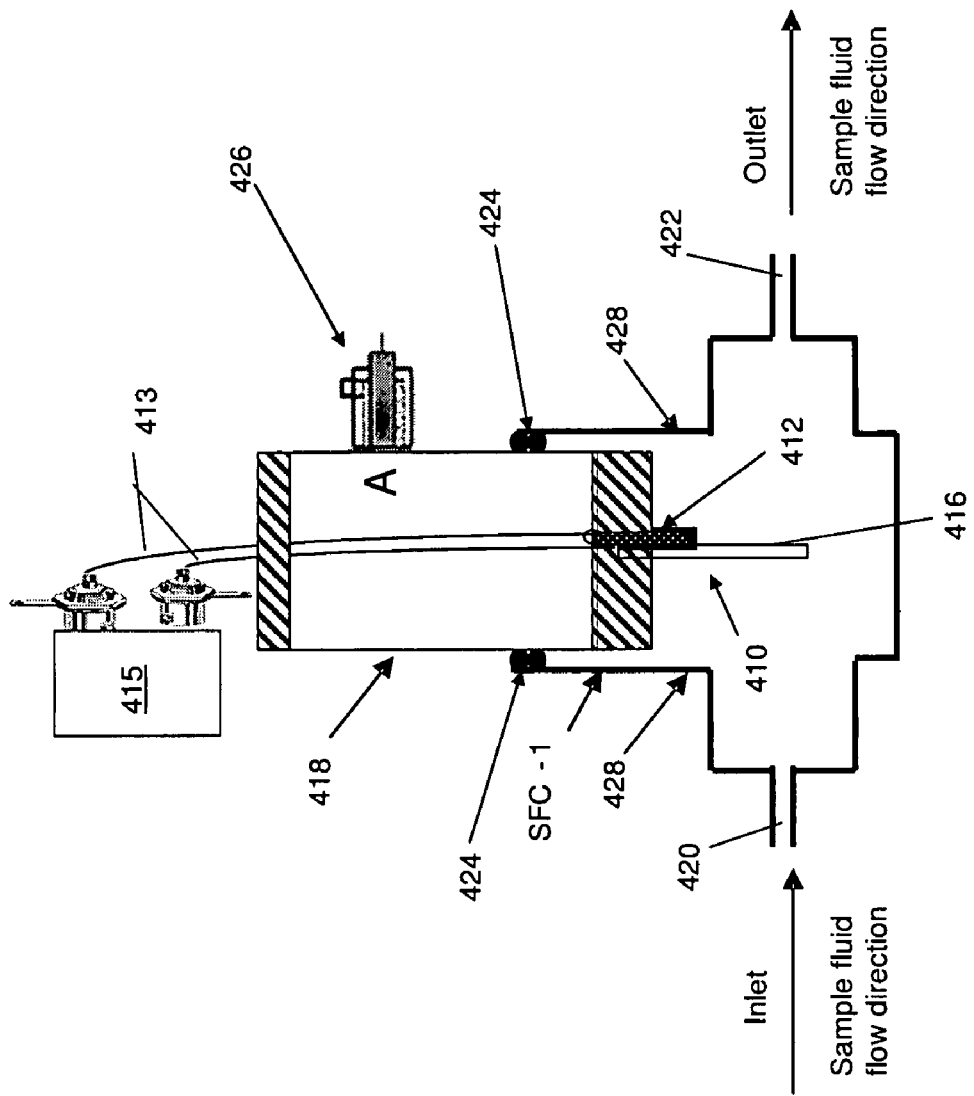
FIG. 4 shows an exemplary flow cell sensor flow cell (SFC) design that can be used with mechanical techniques of removal or prevention, including those described herein.

An exemplary method of exposing a sensor to a medium is to position the sensor in a flow cell configuration. FIG. 3 illustrates the use of the SPR based sensor positioned adjacent to a flow cell. FIG. 4 illustrates the use of a sensor flow cell with a piezoelectric cantilever sensor positioned inside the flow cell. It is noted that there are a plurality of configurations that can be used with the described techniques and only an exemplary setup is described herein. Other configurations may include alternate geometrical configurations, for example, of the sensor or the flow cell configurations.

A sensor flow cell (SFC) 400 that may be used with the removal and prevention techniques with a piezoelectric cantilever sensor is shown in FIG. 4. Flow inlet 420 and flow outlet 422 are positioned at the lowest point of the non-piezoelectric layer 416 to provide horizontal sample flow perpendicular to the lowest portion of sensing surface 410, though positioning of the flow inlet 420 and flow outlet 422 at different heights is also possible. O-rings 424 or a suitable fitting may be provided to seal the SFC flow cell 400 to the sensor casing 418. The two surfaces of piezoelectric layer 412 may be connected via electrical wires 413 to a suitable measuring device 415. An ultrasonic device 426 may be attached in any suitable manner to the sensor flow cell 400.

A binding agent for the target material is immobilized on sensing surface 410 of non-piezoelectric layer 416. In SFC, sensing surface 410 is shown positioned perpendicular to the sample flow direction. Contacting the sample with the sensor can be accomplished by flow of the sample relative to the sensor. Sometimes, flow alters the frequency response of a piezoelectric cantilever sensor in an unsystematic manner by introducing noise and perturbations. The use of the flow cell with the described removal techniques is useful because it minimizes settling due to density variations and does not compromise the sensitivity of the piezoelectric cantilever sensor.

The flow cell provides an exemplary setup for exposing a sensor to a medium. Electrical means, such as electrodes, or ultrasonic means, such as sound vibrations, can be utilized to perform the removal or prevention techniques. The experimental setup also provides the capability to modify the flow rate to have a velocity that can remove material that has accumulated on the sensor surface or cause fluid motion that prevents material from attaching to the surface.

Figure 5:
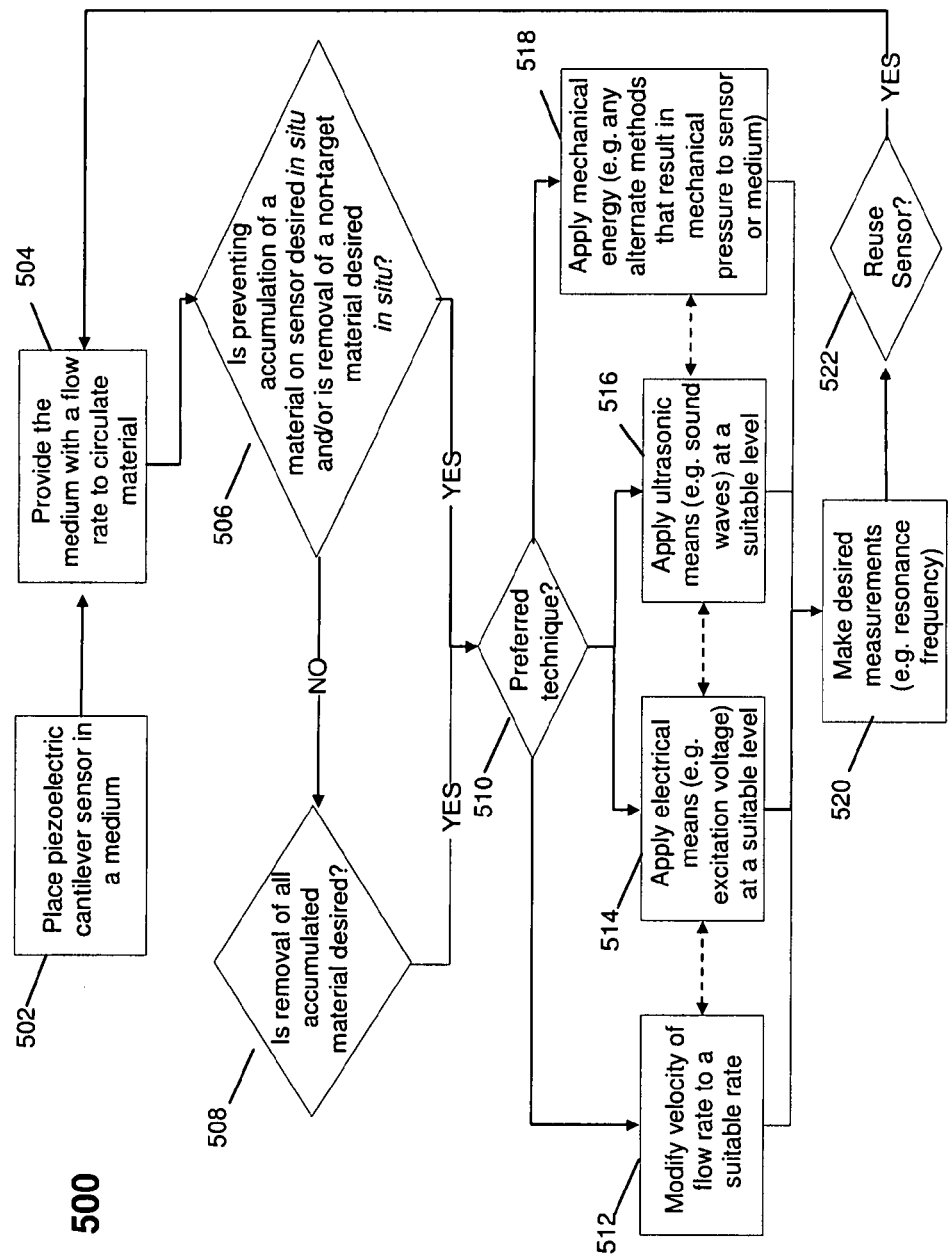
FIG. 5 shows a flow diagram of an example process for removing material that has accumulated on the surface of a piezoelectric cantilever sensor or for preventing material from accumulating on the sensor surface.

FIG. 5 illustrates a flow diagram that sets forth an example utilization of the removal and/or prevention techniques described herein as utilized with a piezoelectric cantilever sensor. A piezoelectric cantilever sensor is commonly coated with gold before exposing the sensor to a medium. Other coatings may be used, such as amine acids, for example. At step 502, the coated or uncoated piezoelectric cantilever sensor is exposed to a medium.

An example method of exposing the piezoelectric cantilever sensor to a medium is to position it in a sensor flow cell (SFC) configuration (as described above). But any method that immerses or exposes the piezoelectric cantilever sensor to a medium can be used.

The medium chosen may be used for the purposes of detecting target materials and further, measuring the amount of a target material in the medium. For the purposes of this example, the medium contains both a target material and a non-target material. It is not required to refine the medium that will be used before exposure to the sensor. The medium does not require the traditional step to refine the medium before using a sensor to take measurements of a target material in a medium. Thus, the medium is not refined before exposing the piezoelectric cantilever sensor to the medium. Refining the medium may require sample preparation or the use of labeled reagents. Refining the medium is not necessary considering that the removal and prevention techniques can prevent adsorption of non-target material. At step 504, the material is circulated within the configuration that exposes the piezoelectric cantilever sensor to the refined or unrefined medium. The circulation, which can be accomplished using a flow cell configuration, increases the likelihood that the target material will come into contact with and accumulate on the surface of the piezoelectric cantilever sensor.

Next, steps 506 and 508 are the decisional steps that decide how the test or experiment will proceed. Oftentimes, both target material and non-target material will attach to the surface of a piezoelectric cantilever sensor. It may be desired to prevent some of the non-target material from accumulating on the surface to the extent possible or, if a non-target material has accumulated, it may be desired to remove that non-target material. It may be desired to accomplish this prevention or removal in situ. In this way, the techniques can be utilized while the sensor is still immersed in the medium. The sensor does not have to be handled unnecessarily and the medium with the target material can continue to be circulated if so desired. Accordingly, step 506 asks "is preventing accumulation of a material on sensor desired in situ or is the removal of a non-target material on a sensor desired in situ?" If the answer to step 506 is NO, the flow diagram proceeds to step 508. At step 508, the question asks "is the removal of all accumulated material desired?" If the answer to step 508 is NO, then the procedure is complete for the purposes of illustrating the techniques described herein and the next step is to take desired measurements at 520.

Typically, the answer to step 506 is YES when it is desired to prevent the non-target material in the medium from interfering with the detection or measurement of the target material. The same goes for removing non-target material. If non-target material is prevented from accumulating or removed from the sensor, more sites are left available for target material. The prevention and removal techniques provide for more accurate mass measurements of target material. Typically, step 508 is answered YES when it is desired to re-use the sensor. For example, once an experiment is complete it may be desired to re-use the sensor or verify mass measurements. Or, if the medium doesn't indicate that it contains target material and a new medium will be circulated, it may be desired to remove any accumulated material from the sensor and start over.

If the answer to either of steps 506 or 508 is YES, then the procedure moves to step 510. At step 510, there are four techniques to choose from to achieve the desired results. The desired results may be to 1) prevent material from accumulating on the piezoelectric cantilever sensor in situ and/or remove at least some of the material on the piezoelectric cantilever sensor in situ, or 2) remove all of the material that has accumulated on the piezoelectric cantilever sensor.

To achieve the desired results, step 512, provides for the technique that uses electrical means, such as an electrical signal or excitation voltage to achieve the desired results. As described in the Experimental Results section, varying the frequency of the electrical signal to the piezoelectric cantilever sensor may result in preventing some material from attaching to the sensor surface. The technique may also work to "shake off" or remove non-target material, and at a certain frequency or voltage, all of the accumulated material could be removed or "shaken off". Similarly, step 514 provides for a technique that involves modifying the velocity of the flow rate of the medium. Step 518 provides the step that applies ultrasonic means. Step 518 provides, in general, the option to apply any suitable alternative method of applying a mechanical energy to the sensor or medium. Any mechanical energy that can be applied to the sensor or the medium to prevent accumulation or release material that has accumulated on the surface of the piezoelectric cantilever sensor may be utilized.

At any point, any of these techniques may be employed separately or in combination, as represented by the dashed lines connecting each of the techniques. For example, consider a medium with both target and non-target materials present that is circulated in a flow cell with a piezoelectric cantilever sensor positioned inside. The technique shown in step 512, modifying the flow rate, may be employed in a manner so that non-target weak adsorbers never slow down enough to allow bonding to the piezoelectric cantilever surface. At the same time, the ultrasonic means of step 516 may be employed to produce high-frequency sound waves that result in a vibration to the sensor or the medium in which the sensor is immersed. These sound waves may be utilized to produce a vibration that "shakes off" weak, non-target adsorbers, thereby achieving removal of certain material. Target material is still able to accumulate on the surface of the piezoelectric cantilever sensor and desired measurements may be taken. Then, as an example, at the completion of the experiment, step 516 may be employed and an excitation voltage at a suitable level may be applied to the piezoelectric cantilever sensor to weaken the attachment of all material that has accumulated on the surface of the piezoelectric cantilever sensor, including both target and non-target material.

Once the chosen techniques are applied, the desired measurements may be taken at step 520. Then, at step 522, the option remains to re-use the sensor. If all of the accumulated material was removed as a result of step 508, the cleaned sensor may be re-used. Similarly, if only some material was prevented from accumulating or removed from the sensor, the sensor can be re-used for continued experimentation.

Step 514 in FIG. 5 sets out the option of using electrical means to achieve the desired results. In an example setup for use with the removal and prevention technique via mechanical means, electrodes may be connected to a sensor, as shown connected to a piezoelectric cantilever sensor in FIG. 2. Electrical means, such as electrodes, may be used with a sensor to cause a vibration to the sensor. When used with a piezoelectric cantilever sensor, electrodes 212, shown in FIG. 2, can be used for both sensing and actuating means. The electrodes may be used to send an electrical signal to the sensor, as well as receive an electrical signal from the piezoelectric portion.

A self-exciting piezoelectric cantilever sensor has a baseline resonance frequency, which can be measured based on the signal received from the piezoelectric cantilever sensor. When mass accumulates on the surface of a self-exciting piezoelectric cantilever sensor, the resonance frequency changes. The measure of the resonance frequency due to the sensor mass itself or the mass that has accumulated on the sensor can be measured based on the sensing voltage that is induced by the piezoelectric portion of the sensor. The prevention of material attaching to the sensor surface, or the release or break of weak material attached to the surface, may occur at the resonance frequency, since the vibration, or acceleration, of the sensor surface, hat a greater occurrence at resonance under those conditions. Varying the excitation voltage may also result in a change to the piezoelectric cantilever sensor's resonance frequency. For example, an increase in voltage or exciting the sensor by applying an alternate electric field across the piezoelectric layer will change the resonance frequency because of the mass of the medium that is moved by the sensor. For example, the change in resonance frequency may be accomplished by increasing the voltage, making it higher than the sensing voltage. The actuating frequency, or the new resonance frequency that is a result of the excitation voltage, may also prevent material from attaching to the sensor surface and/or release non-target material that has attached to the surface. In fact, increasing the voltage may result in a resonance frequency that unbinds all of the material, non-target and target, attached to the surface.

When the medium is subjected to electrical pressure, such as an excitation voltage, an oscillation of the sensor or medium may result. If the electric field applied is alternated periodically, the sensor will vibrate. The result of a vibration of the sensor or medium due to a varied frequency is that, at certain frequencies, the bonds of any material bonded to the surface of the sensor may break or be weakened to the point of release. At other frequencies, materials that have a weaker bond to the surface may be released due to the resulting vibration, such as non-targeted materials that are removed to improve mass measuring techniques. Certain frequencies may also prevent some materials from attaching at all to a sensor surface.

Electrodes 212 shown in FIG. 2 can be used to apply the excitation voltage to a sensor, as described above with a piezoelectric cantilever sensor. Electrodes, or any appropriate means (e.g., inductive means, wireless means), can be utilized to cause a vibration of the sensor or the medium. The Experimental Results section below describes specific experiments utilizing the electrical means technique.

Step 512 in FIG. 5 sets out the option of using a modified flow rate of the medium to achieve the desired results. Flow improves transport of material to the sensor surface thereby increasing the probability of target material binding to the fixed binding area of the sensor and thereby facilitating detection of lower concentrations of target material in a sample volume. But also, at certain velocities of the fluid, the flow can cause a mechanical motion of the medium and/or the sensor. The disturbance to the medium or the modified flow rate of the medium can result in a vibration of the sensor or the medium. An exemplary flow cell configuration that was used in experiments is shown in FIG. 4.

The velocity of the fluid in the SFC may be modified, for example, by changing the flow rate, changing the laminar velocity, or causing a greater turbulent force of the medium within the flow cell. Changing the flow rate may involve changing the fluid rate as the fluid flows into inlet 420. Turbulent flow is characterized by causing irregular movement of particles of the medium. The laminar velocity of the medium is the movement of the medium in definite and observable paths, for example, around the sensor positioned in the flow cell. The laminar velocity of the medium proximate to the sensor, or the local velocity, may be modified. Medium proximate to the sensor can include medium at any distance from the sensor such that motion of the medium causes motion of the sensor (e.g., distance on the order of µM or mM). Changing the flow cell configuration can modify the laminar velocity or local velocity. For example, in the flow cell example shown in FIG. 4, if the walls 428 of the sensor flow cell were closer together, the velocity of the medium may be increased near the sensor even though the flow rate is not changed. Similarly, the velocity of the medium may change in different portions of the flow cell if the sensor is not centered in the flow cell (as depicted in FIG. 4) and is positioned closer to one of the walls 428.

The resulting motion of the methods used to modify various aspects of the medium velocity can weaken the attachment of material that has accumulated on the sensor. As with the applied excitation voltage, the velocity can be selected so as to cause a vibration of the sensor that releases all of the material bound to the sensor surface. The velocity of the fluid in the flow cell can be chosen so as to release non-targeted materials, thereby increasing the available sites for the targeted material. Also, the flow can be used to cause mechanical motion of the sensor or the fluid that prevents the attachment of some materials to the sensor altogether.

A flow cell configuration was used in example embodiments to apply the modified flow rate. It is noted that this technique may be accomplished by other configurations and may be employed in any medium (e.g. by increasing the movement of molecules in a gaseous medium).

Other means may be utilized to inject mechanical energy to the surface of a sensor. For example, ultrasonic means is another example of a method that uses mechanical energy to perform the techniques described. For example, if sound vibrations are employed via ultrasonic means into a liquid, an ultrasonic transducer may be utilized to convert high frequency electric energy into mechanical motion or ultrasound vibrations. High frequency sound waves may be produced, usually above 20 kHz. The high-frequency sound waves may result in a vibration to the sensor or the medium in which the sensor is immersed.

The measurements taken during exposure of a sensor to a medium, which are then compared to measurements taken after the removal or prevention techniques are employed, may be used to verify the accuracy of the target mass measurement. For example, binding of a material to the non-piezoelectric portion of the self-exciting, self-sensing piezoelectric cantilever sensor results in a change in mass of the self-exciting, self-sensing piezoelectric cantilever sensor, a change in stiffness of the self-exciting, self-sensing piezoelectric cantilever sensor, or a combination thereof. The piezoelectric cantilever sensor experiences flexural oscillations and the sensor resonates when the excitation frequency matches the natural frequency of the cantilever sensor.

The changes in mass and/or stiffness of the piezoelectric cantilever sensor are measurable as changes in resonance frequency, and can be monitored and measured by an appropriate analysis device, such as an operational amplifier, an impedance analyzer, a network analyzer, an oscillator circuit, or the like, for example. If the resonance frequency is monitored as material accumulates on the sensor, the change in the resonance frequency as the material is released from the sensor using the techniques described herein can be used to verify that material has been released. Removing the bound material provides a method of determining that the sensor response is due to attachment of the targeted If a surface plasmon resonance based sensor is used for detecting mass on the sensor, the measurement is based on the sensor's response to a refractive index near the sensor surface. When material binds to the surface of a SPR sensor, changes in the refractive index of the medium may be measured for mass detection by an appropriate detector. Following the removal and/or prevention techniques described herein, the change in the refractive index and the return of the refractive index to its value before exposure to the medium may be used to verify the accuracy of the mass measured.

With any sensor, an appropriate measuring device may be configured to determine the changes in mass on the sensor. When using a piezoelectric cantilever sensor, for example, an appropriate measuring device measures a first resonance frequency measure of the piezoelectric cantilever sensor prior to exposure to the material. The measuring device is capable of measuring a second resonance frequency of the piezoelectric cantilever sensor subsequent to exposure to the material. Then, after removal of the material, the release of the bound material can be verified via the measuring device if the second resonance frequency returns to the first resonance frequency.

Figure 6:
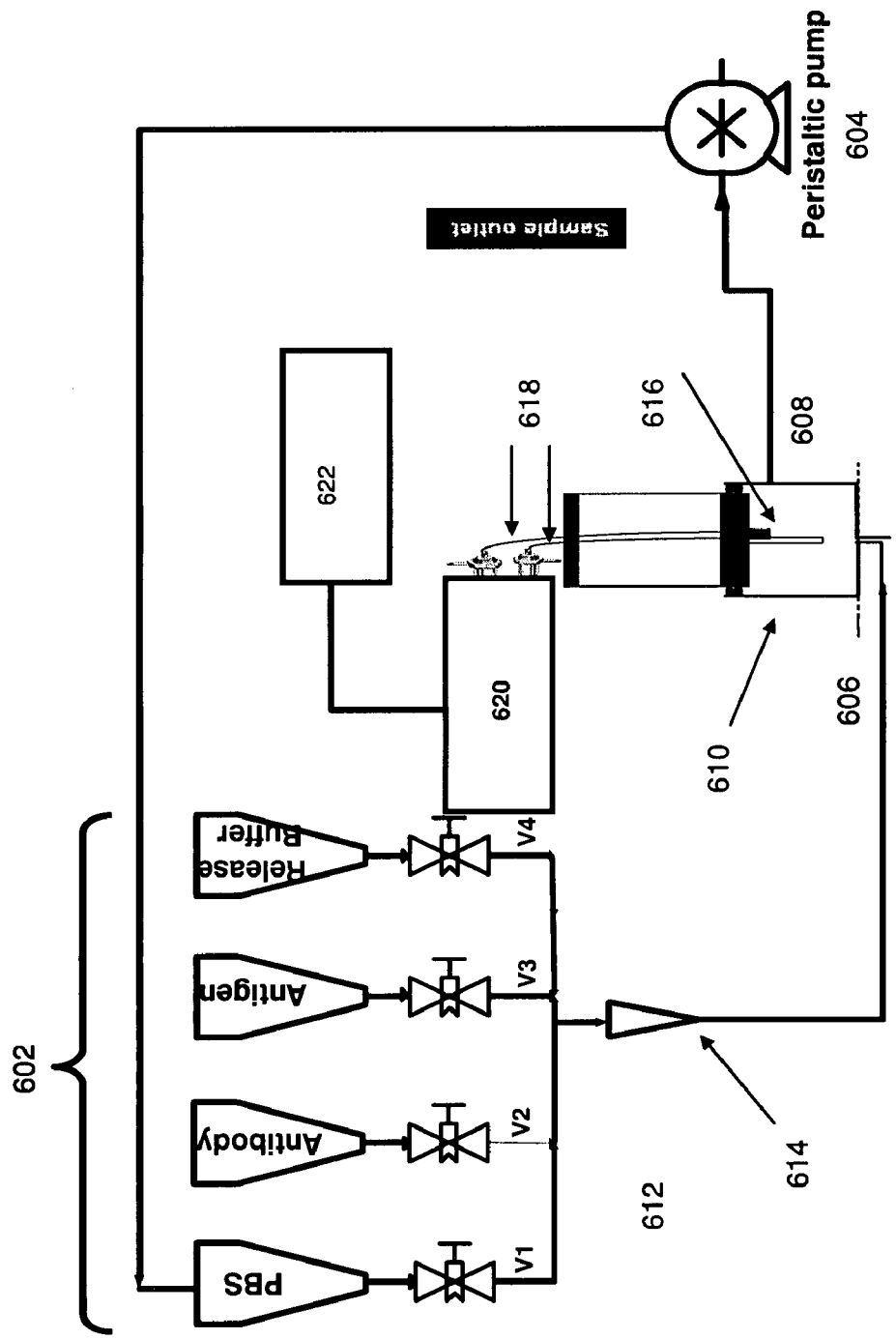
FIG. 6 shows an exemplary sensing system that can be used with that can be used with any of the techniques described.

A schematic of an experimental setup is given in FIG. 6. The exemplary experimental setup consists of four fluid reservoirs 602, a peristaltic pump 604, and a sensor flow cell (SFC) 610 as further described and shown in FIG. 4. The inlet 606 and outlet 608 are located at the bottom and on the side of the cell 610, respectively. The liquid reservoirs 602 are connected to the inlet 606 of the sensor flow cell (SFC) 610 via a five-entrance port manifold 612 with a single outlet 614. The outlet 608 of the flow cell 610 is connected to a peristaltic pump 604, which controls the flow of the desired fluid into and out of the SFC 610.

The functionalized piezoelectric cantilever sensor 616 is secured vertically into the cell 610 filled with a buffer solution; where this setup is shown to use a phosphate buffered saline (PBS). But other buffers may be used, for example MCH or TE buffers. Cantilever electrodes 618 are connected to an impedance analyzer 620 interfaced to a PC 622 with LabVIEW® application for recording impedance and phase angle measurements. The valves (V1-V4) located at the bottom of each of the fluid reservoirs 602 enable the selection of the fluid for flow into the SFC 610 or for circulation. Switching the outlet line from the peristaltic pump 604 into the desired fluid reservoir enables total recirculation, when needed. All valves (V1-V4) can be manipulated manually.

In the experimental setups, each of the four fluid reservoirs 602 is allocated for solutions to be released. Phosphate buffered saline (10 mM, pH 7.4) is shown in this setup and may be used to stabilize the sensor 616 in the flow cell 610. Any solution that can stabilize the environment in the flow cell or create similar density environments within the cell may be used (e.g. phosphate saline buffer (PBS) or Tris-EDTA buffer). An antibody (10 µg/mL), a test sample, and a release solution were each separately contained in three of the fluid reservoirs to run experiments. The SFC 610 may be maintained at a constant temperature by circulating constant temperature water through a jacket surrounding the SFC 610.

The experimental setup here would be initiated by circulating PBS through the flow cell 610 until the cantilever's 616 resonant frequency reached a steady value, which is usually achieved in 10 minutes under these circumstances. Then, activated antibody solution was flowed into the cell (by opening the appropriate valve) after which the flow could be stopped to allow antibody immobilization under stagnant conditions. The PBS (by opening and closing the appropriate valves) may then be used to rinse out the lines. Upon completion of the rinsing step, the antigen solution may be introduced into the sensor flow cell by opening and closing the appropriate valves. At this point, one of the techniques that prevent bonding to the sensor may be employed in this experimental setup to keep certain molecules or non-targeted material off of the sensor. For each of the experiments, the measured resonant frequency was monitored for at least 15 minutes. After the antigen attachment concludes, that valve may be closed and one of the removal techniques could be employed. The time for each step during a detection experiment varies.

Experimental Results

Figure 7:
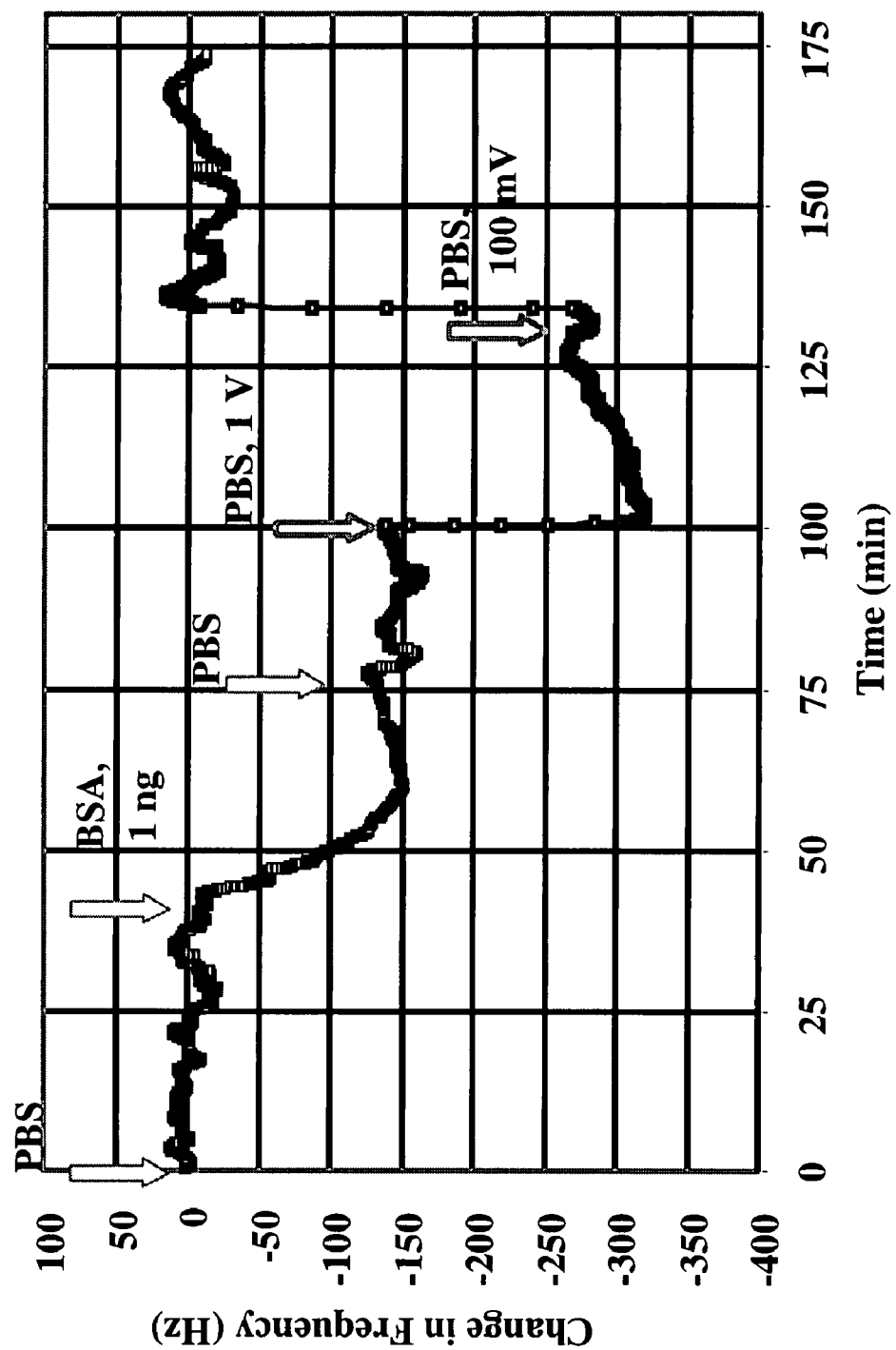
FIG. 7 shows the results of an experiment that mechanically removes bovine serum albumin from the surface of the piezoelectric cantilever sensor in a liquid medium.

Specific experimental results are shown herein that illustrate the effects of mechanical energy as applied to a piezoelectric cantilever sensor. In particular, the effects of applying an excitation voltage were observed. FIG. 7 sets forth the results of an example using an antibody to bond to bovine serum albumin (BSA), the target material. The sensor was first immobilized with the antibody and then flushed with PBS to create an analyte-free environment for the sensor and remove weakly attached and suspended particles. After approximately 25 minutes of allowing for BSA attachment, and a PBS flush, one volt was applied followed by 100 mV excitation. The sensor resonance frequency decreases initially due to the 1V excitation voltage due to the added mass of surrounding fluid. Shortly after that, when the excitation voltage is reduced to 100 mV, FIG. 7 shows that resonance frequency of the sensor returns to its original state. The return of the resonance frequency to its original state indicates that the bovine serum albumin is released from the sensor and the antibody is still fully in tact on the sensor surface.

Figure 8:
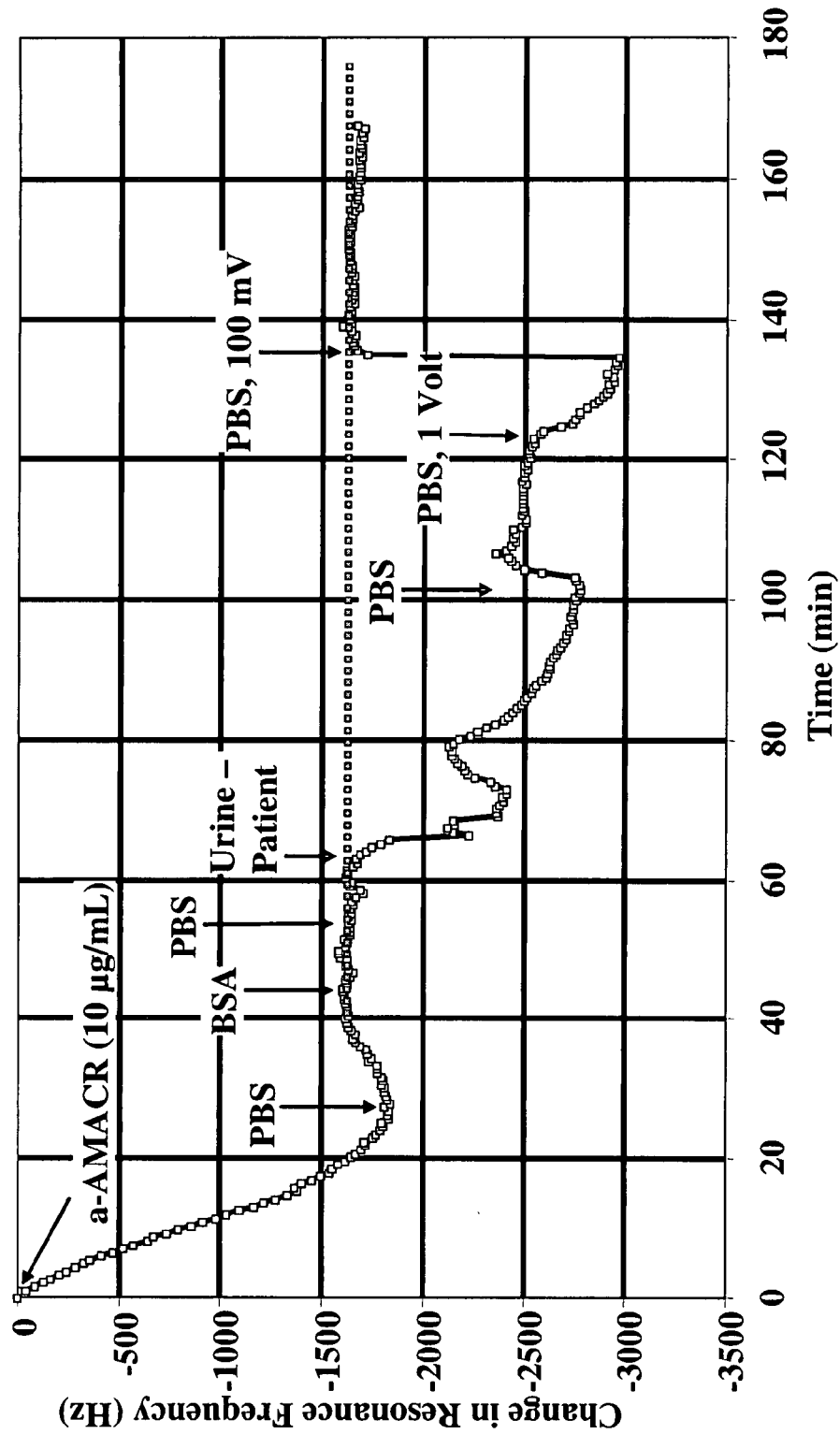
FIG. 8 shows the results of an experiment that mechanically removes prostate biomarkers from urine from the surface of the piezoelectric cantilever sensor in a liquid medium.

FIG. 8 sets forth the experimental results using an applied excitation voltage with anti-AMACR and patient urine with prostate markers. The probe was first immobilized with the antibody anti-AMACR, where AMACR is a prostate biomarker. After approximately 20 minutes, the antibody was immobilized and then phosphate buffered saline (PBS) was introduced into the flow cell to remove all a-AMACR in the flow cell. BSA is then introduced as a blocking agent, and none appears to adsorb to the sensor surface as there is no resonance frequency change. Patient urine bearing the prostate marker, AMACR, was then released into the flow cell which caused a frequency shift down as the markers bonded to the antibody on the sensor surface. After almost an hour of allowing for antigen attachment, one volt was applied followed by 100 mV excitation. FIG. 8 shows that the sensor returns to its original state, post antibody immobilization. The horizontal dotted line indicates the closeness of recovery. The resonance frequency indicates that the antibody (a-AMACR) is still fully in tact on the sensor surface. This experiment was done repeatedly with the same sensor, receiving similar results. The piezoelectric cantilever sensor was still in tact following these experiments. This indicates that the detection performance of the piezoelectric cantilever sensor to be reused was not degraded.

Figure 9:
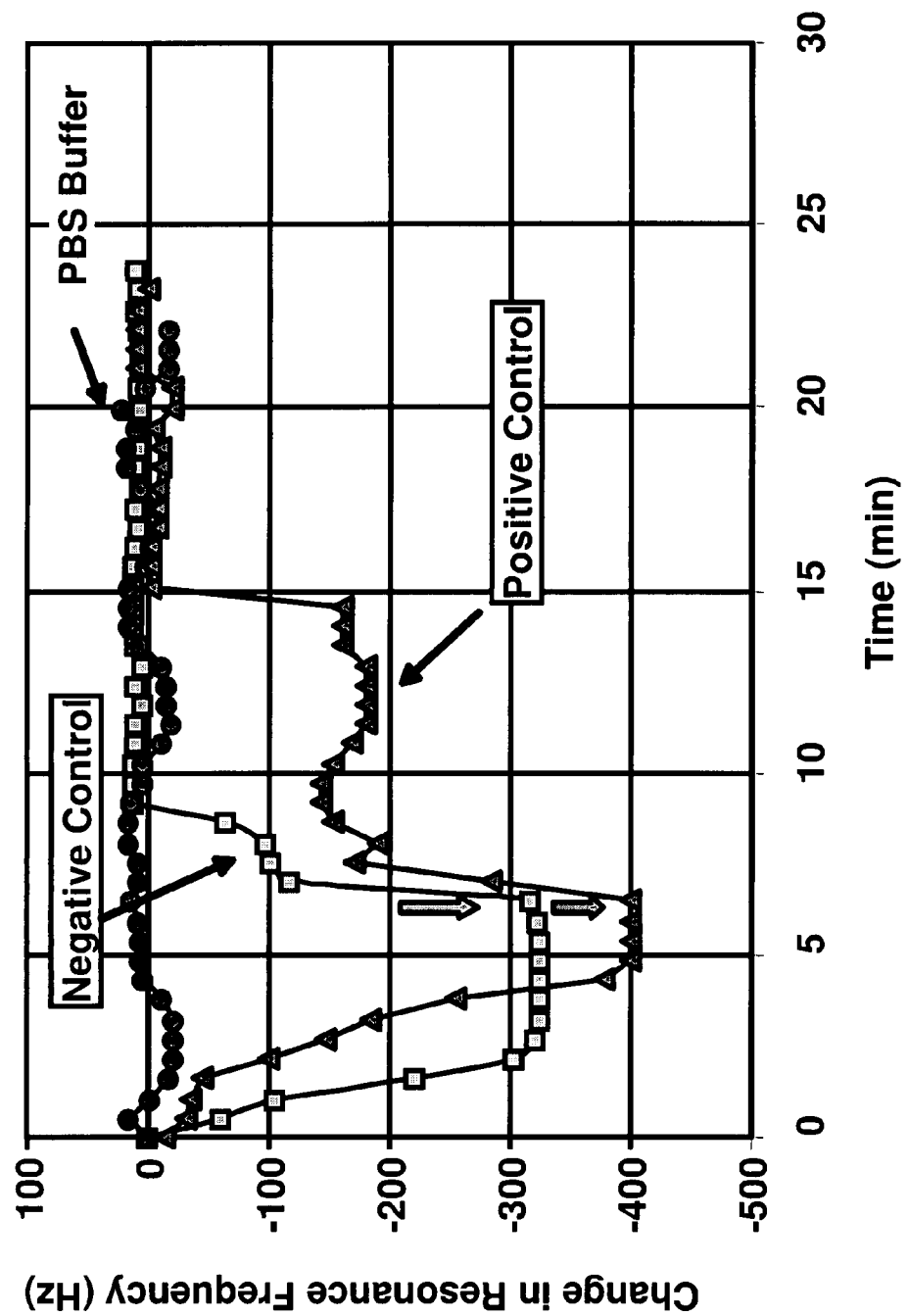
FIG. 9 shows the results of an experiment that mechanically prevents proteins, salts, and other biomaterials present in human urine from accumulating on the surface of the piezoelectric cantilever sensor in a liquid medium.

Some material does not attach at all to a cantilever sensor that has any or a low vibration and non-specific adsorption is generally weaker than the binding energy between the antibody and target antigen. FIG. 9 shows the experimental results of the prevention technique for an experiment with human urine. Human urine did not attach to the cantilever sensor surface that was vibrating at 100 mV. Positive, negative, and buffer controls were used. The positive control (shown by the triangle) shows the response of a clean sensor (no antibody) exposed to AMACR-free urine from a young adult male spiked with 100 ng/mL of AMACR followed by a PBS rinse. The negative control (shown by the squares) shows the response of antibody-immobilized PEMC sensor to a one-mL sample of control young-male adult urine (AMACR-free) at 0.5 mL/min followed by a PBS rinse. The buffer control (shown by the circles) was an a-AMACR antibody-immobilized sensor exposed to PBS at 0.5 mL/min.

The typical responses given in FIG. 9 shows the positive and negative control samples undergoing a sharp decrease during the first 5 minutes of introducing the urine sample due to density difference between urine and PBS, followed by stabilization at a constant resonance frequency. A PBS flush caused the removal of recirculating urine, and the resonance value returned to the pre-control resonance value. The sensor response returned back to the original resonance frequency value indicating that no material from urine attached to the sensor. Positive and negative controls yielded a zero response of $-9\pm13$ and $-34\pm18$ Hz, respectively. This advantageous feature is due to the continuous sensor surface vibration that was applied during the piezoelectric cantilever sensor based measurements.

Similar results show that urinary proteins and compounds, plasma proteins, and proteinous and fat material in beef washes do not adsorb on both antibody-prepared sensor or on gold-coated sensor in the flow field.

Figure 10:
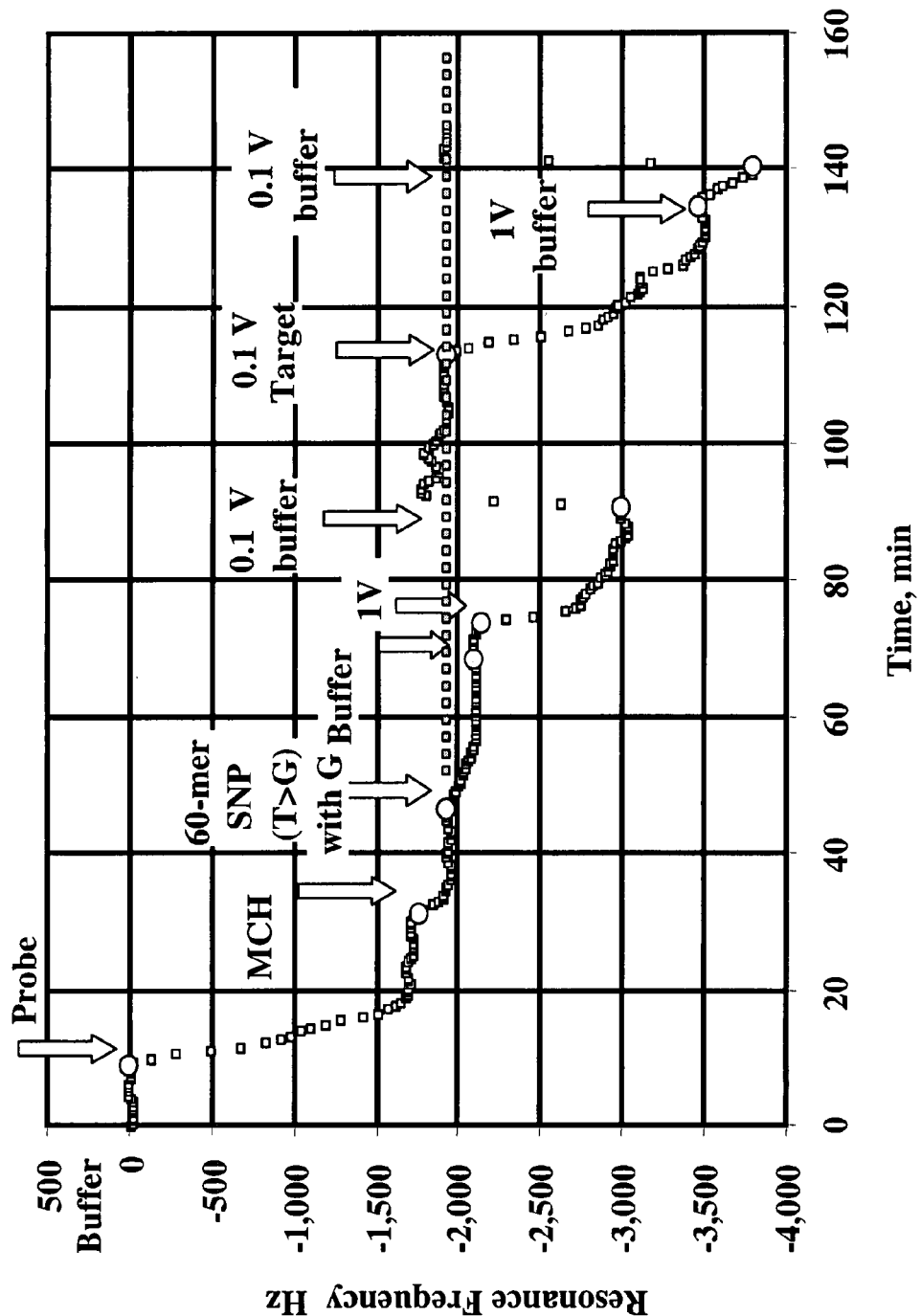
FIG. 10 shows the results of an experiment that mechanically removes partially and fully hybridized single stranded DNA from the surface of the piezoelectric cantilever sensor in a liquid medium.

FIG. 10 shows an experiment using the removal techniques in a liquid medium. In this experiment, the sensor was coated with gold (Au). Then, the probe ($HSC_6H_{12}$-5'GGA AGA AGC TTG CTT3') is immobilized (1 pM, 2 mL) that causes a1720 Hz shift down, followed by MCH (1 µM, 2 mL) to stabilize the probe and to fill in empty sites. At 46 min, 2 mL of 10 pM 60-mer Single Nucleotide Polymorphic strand with T>G mismatch (indicated by T>G) 5'-ACC CGT CCG CCA CTC GTC AGC AAA GAA GCG AGC TTC TTC CTG TTA CCG TTC GAC TTG CAT-3' is introduced (bold indicates the hybridization region), and it causes a weak hybridization with a response of 160 Hz. After a buffer flush, excitation voltage is increased to 1 V, and the sensor responds by decrease in resonance frequency due to added mass of surrounding fluid and shortly after that excitation level is reduced to 0.1 V and resonance frequency increases to pre-hybridization value; horizontal dotted line indicates the closeness of recovery. We then introduced 2 mL of 10 pM 60-mer complementary strand, and strong hybridization occurs with ~1580 Hz shift down. At 133 min, excitation again is increased and then it is returned to 0.1 V, and one notes the recovery is back to $-1920$ Hz which is within experimental error to prehybridization value of $-1938$ Hz, and is indicated by the dotted horizontal line.

Figure 11:
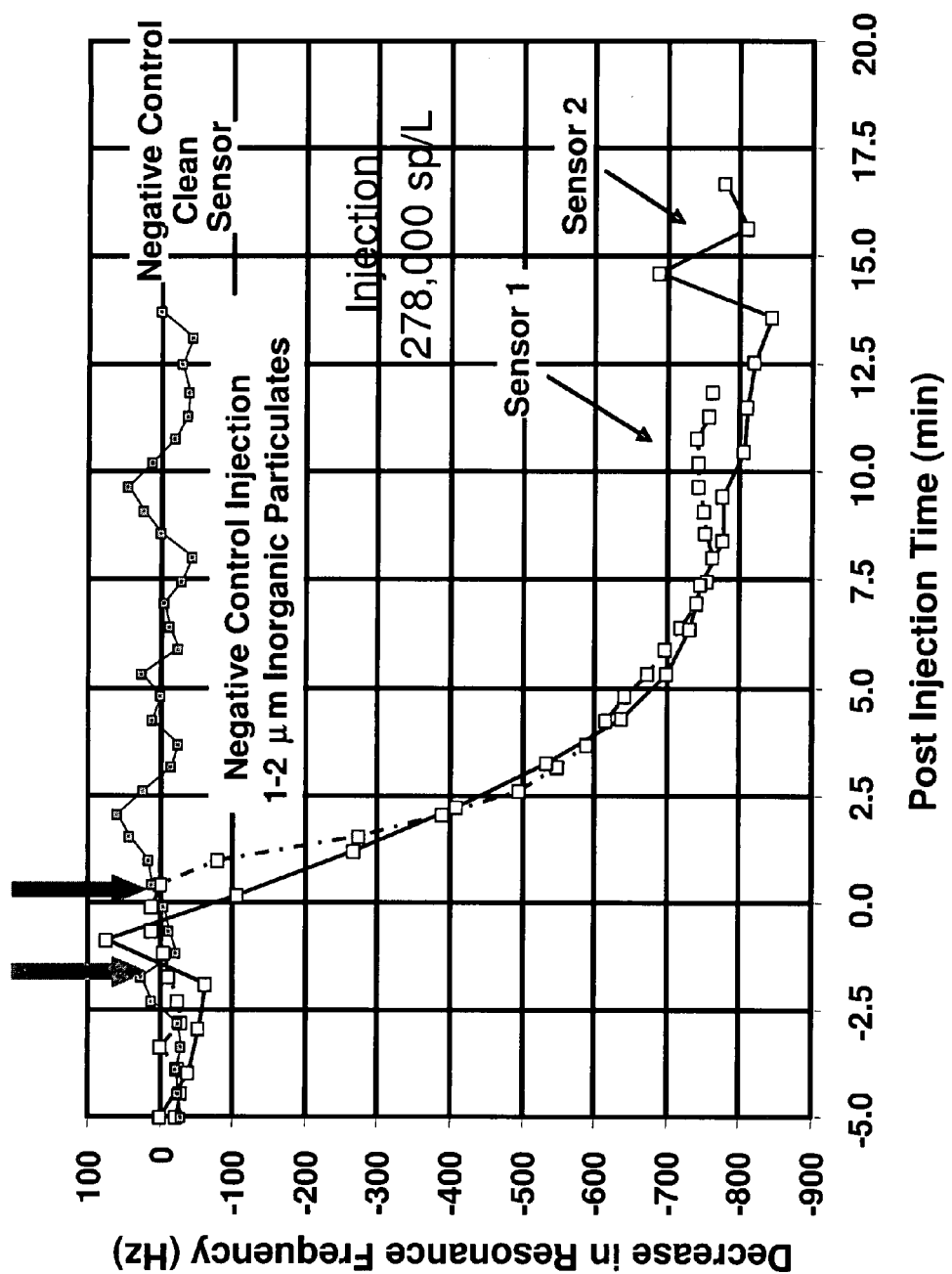
FIG. 11 shows the results of an experiment that indicates that certain particles (e.g. alumina silicate) do not attach to sensor immobilized with an antibody in a gaseous material.

FIG. 11 shows the results of multiple experiments using the removal techniques in a gaseous medium. FIG. 11 shows the frequency response of a piezoelectric cantilever immobilized with antibody to bond Bacillus anthracis (Sterne strain; BA)) to various concentration of BA bioaerosol. In each experiment shown in the graph, a steady state frequency response of the sensor was achieved initially by flowing humid air (RH=85±3% and T=23±0.3° C.) at a flow rate of 2.4 liters per minute. Nebulizer charge was 10 million spores in 4 mL and nebulized for 15 minutes which yielded gas phase concentration of 278,000 spores/L of air. The response was immediate as is seen in the figure.

Two-similarly constructed sensors (labeled Sensor 1 and Sensor 2) gave nearly identical response. Subsequent to BA detection, each sensor was removed and placed in a flow apparatus, then buffer (PBS) flow was followed by a pH 2.2 solution. Release occurred rapidly over a five minute period and the recovery of the resonance frequency was half of the change observed in air (data not shown). This is an expected result as the effective mass of the cantilever sensor is a function of fluid density. In one of the repeat runs, the sensor surface was sputter coated with platinum and then examined on a Field Emission Environmental Scanning Electron Microscope (FEESEM). Micrographs showed sparse attachment on the sensor. Finally, the sensor's resonance frequency in vacuum (60 mTorr) was ~1 kHz lower compared with pre-detection value, which also confirmed BA attachment.

Thus, three different methods with two repeat experiments confirmed the detection of BA spores in gas phase under flow conditions. The controls consisted of two types. In the first, we installed a clean sensor (no antibody on surface) and repeated BA injection, and the response shown in FIG. 11 gave a slightly noisy response, but no significant change. Second, to test the antibody-immobilized PEMC response to particulate matter and non-specific adsorption, we injected in the flow apparatus alumina silicate particles (Duke Scientific Corp., Palo Alto, Calif., cat. No. 235; size 0.2 to 6.0 µm; density=2.5 g/cm$^3$). The particulate matter was suspended in DI water (0.75 mg/mL), and one mL was injected into the nebulizer containing 3 mL of DI water to give an injection concentration of 0.19 mg/mL. The vaporization rate was 0.2 mL per minute into 2.7 liters/min dry air giving an airborne concentration of 14 µg/L-air, a value that is comparable to dust concentration at street level. The system was run until the nebulizer was dry. During this time there was no discernable decrease in resonance frequency (labeled as "-ve control injection" in FIG. 11) which demonstrates that the sensor is not influenced by the presence of inorganic particles in the air. Upon examination under microscope, surface particle concentration was not any different from control which had gone through a detection experiment (n=7). FIG. 11 shows that alumina silicate particles did not adsorb or attach to the PEMC sensor surface.

Figure 12:
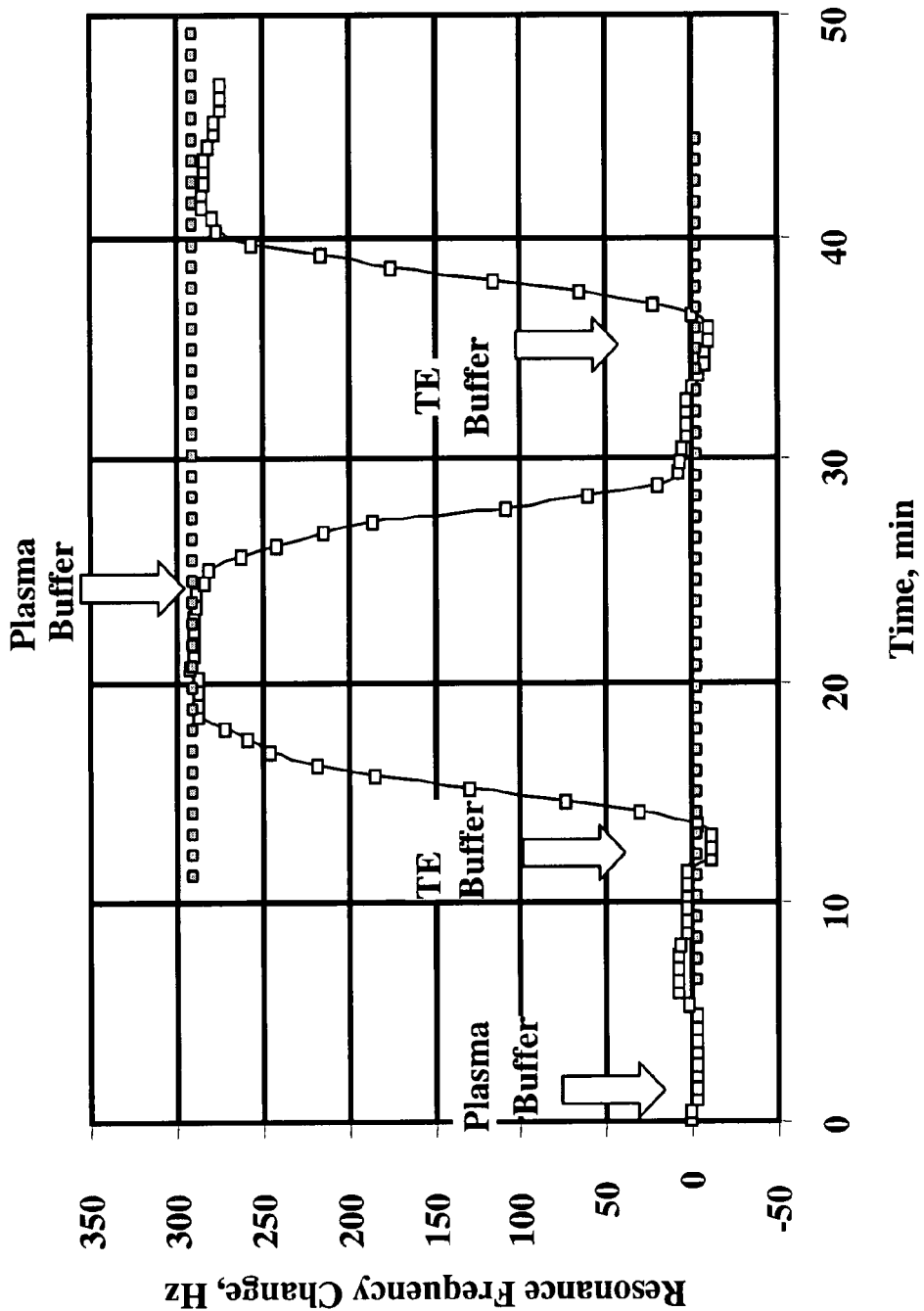
FIG. 12 shows the results of an experiment with a piezoelectric cantilever sensor prepared with single strand DNA, indicating no non-specific adsorption of non-target material.

FIG. 12 illustrates an experiment showing that no non-specific adsorption occurs on a surface prepared with single strand DNA or MCH. The experiment utilized a piezoelectric cantilever sensor that was prepared with 49 pM probe and 1 µM MCH. Plasma buffer was introduced in a once through flow mode. After a stable resonance frequency was reached, flow was changed to TE buffer at t=13 min, and to plasma buffer at t=25 min and then to TE buffer again at t=36 min. The response is reversible and recovery is within 10 Hz. Time taken to respond was ~5 minutes. Given that hold-up volume of the flow circuit is 2.2 mL, and the flow rate is 0.6 mL/min, the transition time indicates the time needed to homogenize the fluid environment surrounding the sensor.

Figure 13A:
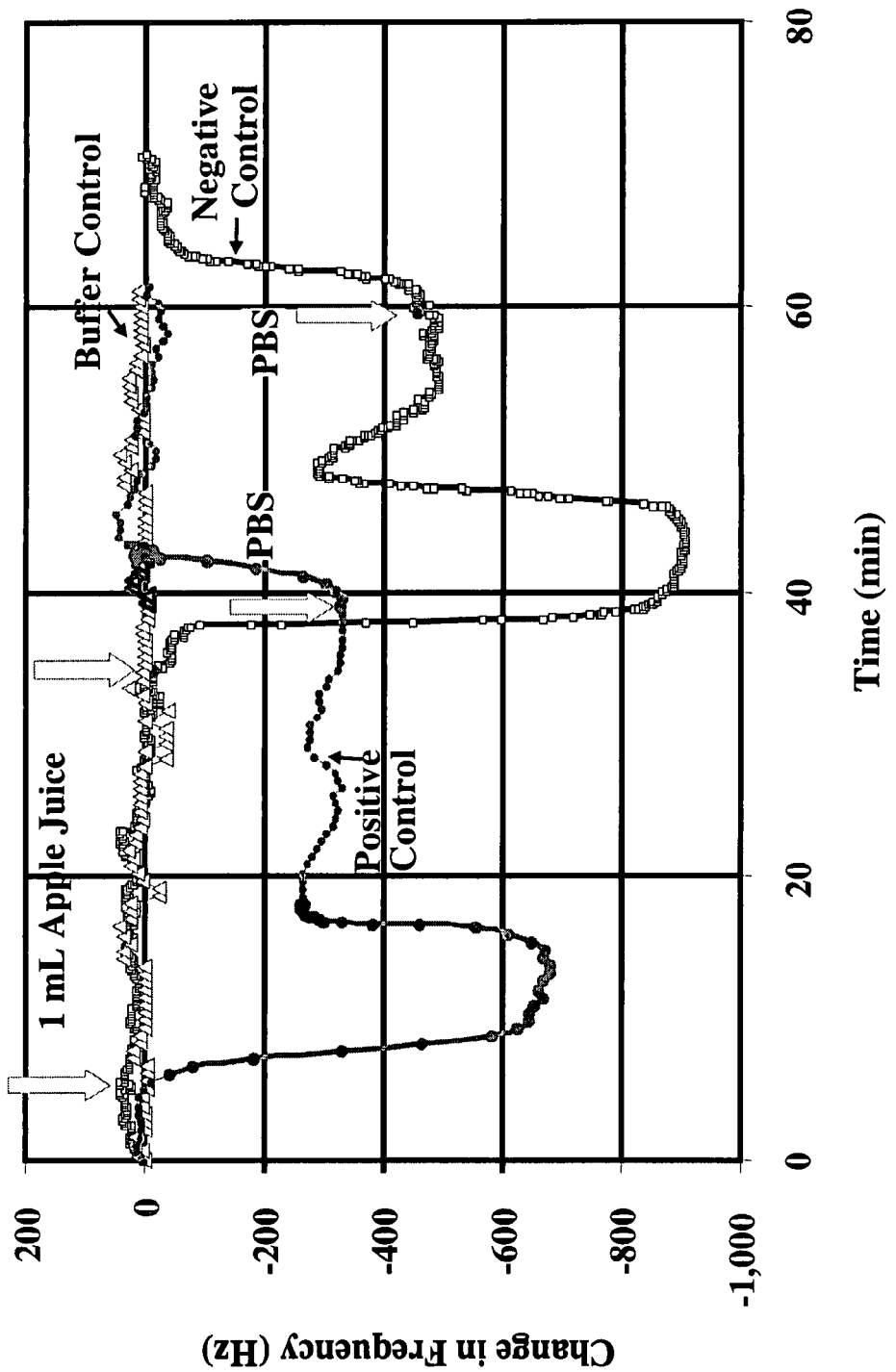
FIGS. 13A and 13B show the results of an experiment using 3 control buffers, indicating that proteinous matter does not adsorb on a coated sensor.
Figure 13B:
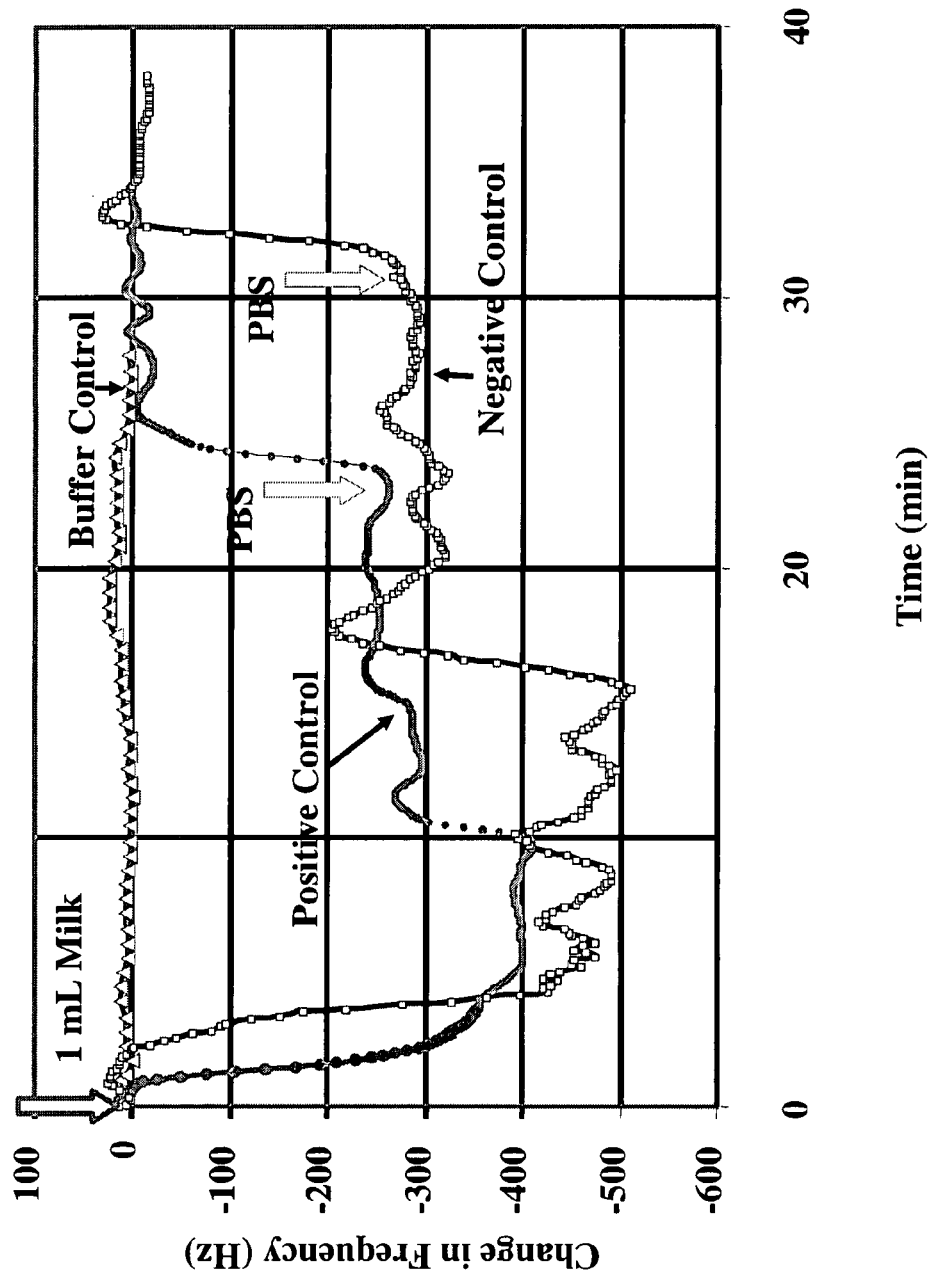

FIGS. 13A and 13B illustrate the resonance frequency shift for three controls, a positive control shown by dots, negative control shown by squares, and buffer control shown by triangles. In both FIGS. 13A and 13B, the results show that proteinous matter does not adsorb on a sensor prepared with a sputtering of gold. Other coatings may be used, such as G, or Ab. In FIG. 13A, the positive control was the response of a piezoelectric cantilever sensor that was not prepared with an antibody to *Staphylococcal* Enterotoxin B (SEB) and exposed to apple juice followed by a PBS rinse. Apple juice is a highly acidic, simple fluid that contains a wide molecular weight range of soluble saccharides. Negative control was the response of an anti-SEB immobilized piezoelectric cantilever sensor to a one-mL apple juice followed by a PBS flush. The PBS buffer control was an anti-SEB immobilized cantilever in PBS (pH 7.4) All experiments were done at 0.5 mL/min. FIG. 13B demonstrates the resonance frequency shifts for the same three controls in milk. Milk is a more complex fluid than apple juice, containing many proteins, fat, and carbohydrates.

As shown in FIGS. 13A and 13B, the positive and negative control showed a sharp decrease immediately following introduction of the medium during the first 5 minutes due to density differences between apple juice (or milk in FIG. 13B). The response stabilized to a constant value as the juice, or milk, became blended with the running buffer, PBS. In order to determine if any of the material in the medium adsorbed to the sensor surface, PBS was introduced to flush the system. As seen in FIGS. 13A and 13B for apple juice and milk, respectively, the resonance frequency recovered back to the original values. The buffer control containing PBS yielded a near zero response. The results indicate that proteinous matter does not adsorb on a sensor prepared with a coating.

Figure 14:
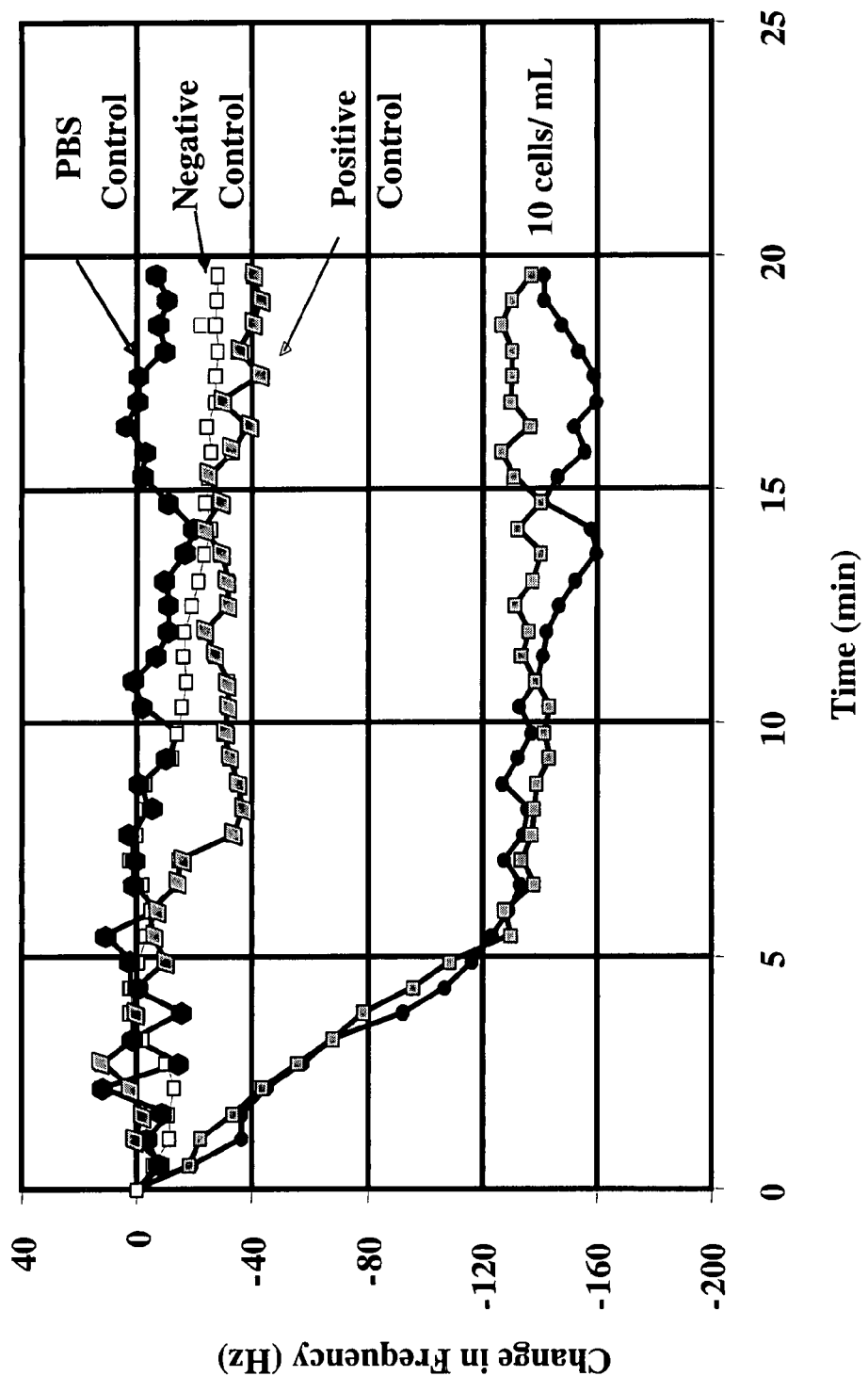
FIG. 14 shows the results of an experiment using a beef wash, indicating that beef wash is not adsorbed on a coated sensor.

FIG. 14 illustrates that material from a beef wash is not adsorbed on a sensor prepared with a coating of gold. Other coating material may be used, such as G, or Ab. The medium that the piezoelectric cantilever sensor is exposed to contains 10 cells/mL of *E. coli*. FIG. 14 shows the resonant frequency response upon binding of the target material to the sensor surface. The control, an antibody-immobilized cantilever in PBS (pH 7.4) at 1.0 mL/min, gave a response of 4±9 Hz. A positive and negative control yielded an essentially zero response of 36±6 and 27±2 Hz, respectively. The positive control (shown by filled squares) was the response of a piezoelectric cantilever sensor to *E. coli* containing target material, but the sensor was not immobilized with the antibody. Negative control (shown by empty squares) was the response of antibody-immobilized piezoelectric cantilever sensor to ground beef in PBS at 1.0 mL/min, but the sample was not spiked with *E. coli*.

Applying mechanical energy to cause sensor vibration or medium disturbance has multiple uses. The sensor can be reused following removal of both targeted and non-targeted molecules, non-targeted molecules can be released, and the result of the vibration may prevent some molecules from bonding to the sensor at all. The mechanical stimulation causes the attachment between the bonding agent to the molecules in the sample to weaken. The removal of the bound molecules in this manner has shown to enable the re-use of the cantilever sensor without degradation of the sensor or the bonding agent.

Applications of piezoelectric cantilever sensors include detection of bioterrorism agents, detection of food-borne pathogens, detection of pathogens in water, detection of cell types in body fluids, e.g. circulating tumor cells, detection of biomarkers in body fluids, e.g. proteins that mark specific pathophysiology such as alpha-fetoprotein, beta-2-microglobulin, bladder tumor antigen, cancer marker CA-15-3, and other CA's, calcitonin, carcinoembryonic antigen, and others, detection of markers of TNT such as DNT, detection of airborne and waterborne toxins, and measurement of the viscosity and density of liquids and gases.

While the removal and prevention of accumulation of material on a cantilever sensor has been described in connection with various embodiments and various figures, it is to be understood that other similar embodiments can be used or modifications and additions can be made to the described embodiments for performing the same function of removal and prevention of accumulation of material on a cantilever sensor without deviating therefrom. For example, the techniques for removal and prevention of accumulation of material on a cantilever sensor also can include any method that causes mechanical motion of the cantilever sensor or of the molecules bonded to the surface. Any method that may be employed so as to use mechanical motion or energy to remove the molecules from the sensor's surface or prevent attachment to the sensor can be utilized. The techniques can be applied at a level that cleans the sensor of all the bound molecules, that releases a portion of the bound molecules, or that prevents at least a portion of molecules from attaching to the sensor surface. Therefore, removal and prevention of accumulation of material on a cantilever sensor should not be limited to any single embodiment, but rather should be construed in breadth and scope in accordance with the appended claims.

What is claimed:

1. A method for controlling accumulation of material on a piezoelectric cantilever sensor, the method comprising:
exposing at least one portion of the piezoelectric cantilever sensor to a medium, wherein the piezoelectric cantilever sensor comprises:
a piezoelectric layer comprising a proximate end and a distal end;
a base portion coupled to the proximate end of the piezoelectric layer;
a non-piezoelectric layer comprising a proximate end and a distal end, wherein:
at least a portion of the piezoelectric layer is coupled to at least a portion of the non-piezoelectric layer such that the piezoelectric layer and the non-piezoelectric layer are not coextensive; and
the base portion is not attached to the non-piezoelectric layer; and
applying mechanical energy to at least one of the medium or the piezoelectric cantilever sensor during exposure of the piezoelectric cantilever sensor to the medium, wherein application of the mechanical energy results in at least one of:
removal of at least a portion of material accumulated on said piezoelectric cantilever sensor; or
prevention of accumulation of material potentially contained in the medium on the piezoelectric cantilever sensor.

2. A method in accordance with claim 1, the medium is not refined before exposing the at least one portion of the piezoelectric cantilever sensor to the medium.

3. A method in accordance with claim 1, wherein:
the piezoelectric cantilever sensor is configured to bind a target material thereto; and
removal of at least a portion of material accumulated on said piezoelectric cantilever sensor comprises removal of at least a portion of a non-target material from the piezoelectric cantilever sensor.

4. A method in accordance with claim 1, wherein:
the medium contains non-target material;
the piezoelectric cantilever sensor is configure to bind at least one target material thereto; and
prevention of accumulation of material potentially contained in the medium on the piezoelectric cantilever sensor comprises prevention of accumulation of at least a portion of a non-target material in the medium on the piezoelectric cantilever sensor.

5. A method in accordance with claim 1, wherein removal of at least a portion of material accumulated on said piezoelectric cantilever sensor comprises removal of at least a portion of material that accumulated on the piezoelectric cantilever sensor during exposure to the medium.

6. A method in accordance with claim 1, wherein applying mechanical energy comprises modifying a local velocity of the medium proximate to the sensor.

7. A method in accordance with claim 1, wherein a source of the mechanical energy comprises an electrical signal applied to the piezoelectric cantilever sensor.

8. A method in accordance with claim 7, wherein the electrical signal comprises a voltage different from a sensing voltage of the piezoelectric cantilever sensor.

9. A method in accordance with claim 1, wherein a source of the mechanical energy comprises ultrasound.

10. A method in accordance with claim 1, wherein:
the piezoelectric cantilever sensor is configured to bind at least one target material thereto;
during exposure of the at least one portion of the piezoelectric cantilever sensor to the medium; concurrently:
detecting target material that is contained in the medium; and
preventing accumulation on the piezoelectric cantilever sensor of at least a portion of a non-target material that is contained in the medium.

11. A method in accordance with claim 1, wherein:
the piezoelectric cantilever sensor is configured to bind at least one target material thereto;
during exposure of the at least one portion of the piezoelectric cantilever sensor to the medium; concurrently:
accumulating target material on the piezoelectric cantilever sensor that is contained in the medium; and
removing at least a portion of at least one non-target material that has accumulated on the piezoelectric cantilever sensor.

12. A method in accordance with claim 1, wherein the medium comprises a first medium, the method further comprising exposing the piezoelectric cantilever sensor to a second medium subsequent to applying mechanical energy to at least one of the first medium or the piezoelectric cantilever sensor, wherein the second medium is different from the first medium.

13. A method in accordance with claim 1, wherein the medium comprises at least one of a liquid, a gas, or a vacuum.

14. A method in accordance with claim 1, wherein the piezoelectric cantilever sensor is a millimeter size piezoelectric cantilever sensor.

15. A method in accordance with claim 1, wherein the piezoelectric cantilever sensor comprises:
a piezoelectric layer comprising a proximate end and a distal end;
a base portion coupled to the proximate end of the piezoelectric layer; and
a non-piezoelectric layer comprising a proximate end and a distal end, wherein:
at least a portion of the piezoelectric layer is coupled to at least a portion of the non-piezoelectric layer; and such that the piezoelectric layer and the non-piezoelectric layer are not coextensive; and
the non-piezoelectric layer comprises the sensing surface.

16. A method in accordance with claim 15, wherein a length of the non-piezoelectric layer is in a range of about 0.1 mm to about 10.0 mm.

17. A method in accordance with claim 15, wherein a length of the piezoelectric layer is in a range of about 0.1 mm to about 10.0 mm.

18. A method in accordance with claim 15, wherein a width of the non-piezoelectric layer is in a range of about 0.1 mm to about 4.0 mm.

19. A method in accordance with claim 15, wherein a width of the piezoelectric layer is in a range of about 0.1 mm to about 4.0 mm.

20. A method for controlling accumulation of material on a sensor, the method comprising:

exposing at least one portion of a sensor to a medium, wherein the sensor is configured to bind at least one target material thereto, the sensor comprising:
- a piezoelectric layer comprising a proximate end and a distal end;
- a base portion coupled to the proximate end of the piezoelectric layer;
- a non-piezoelectric layer comprising a proximate end and a distal end, wherein:
  - at least a portion of the piezoelectric layer is coupled to at least a portion of the non-piezoelectric layer such that the piezoelectric layer and the non-piezoelectric layer are not coextensive; and
  - the base portion is not attached to the non-piezoelectric layer; and
- applying mechanical energy to the sensor to cause sensor vibration in a direction perpendicular to a surface of the sensor, wherein the sensor vibration results in at least one of:
  - removal of at least a portion of material accumulated on said sensor; or prevention of accumulation of material potentially contained in the medium on the sensor.

21. A method in accordance with claim 20, further comprising modifying a local velocity of the medium proximate to the sensor.

22. A method in accordance with claim 20, wherein a source of the mechanical energy comprises an electrical signal applied to the piezoelectric cantilever sensor.

23. A method in accordance with claim 20, wherein a source of the mechanical energy comprises ultrasound.

24. A method in accordance with claim 20, further comprising modifying a local velocity of the medium proximate to the sensor.

25. A method in accordance with claim 20, wherein the medium comprises at least one of a liquid, a gas, or a vacuum.

26. A method for indicating that a material has accumulated on a piezoelectric cantilever sensor, the method comprising:
- exposing at least a portion of the piezoelectric cantilever sensor to a medium, wherein the piezoelectric cantilever sensor is configured to bind to at least a portion of at least one target material thereto, the sensor comprising:
  - a piezoelectric layer comprising a proximate end and a distal end;
  - a base portion coupled to the proximate end of the piezoelectric layer;
  - a non-piezoelectric layer comprising a proximate end and a distal end, wherein:
    - at least a portion of the piezoelectric layer is coupled to at least a portion of the non-piezoelectric layer such that the piezoelectric layer and the non-piezoelectric layer are not coextensive; and
  - the base portion is not attached to the non-piezoelectric layer;
- applying mechanical energy to at least one of the medium or the piezoelectric cantilever sensor during exposure of the piezoelectric cantilever sensor to the medium, wherein:
  - application of the mechanical energy results in at least one of:
    - prevention of accumulation, on the piezoelectric cantilever sensor, of at least a portion of at least one non-target material potentially contained in the medium, wherein at least a portion of at least one target material potentially contained in the medium may still accumulate on the piezoelectric cantilever sensor, or
    - removal of at least a portion of at least one non-target material that has accumulated on the at least a portion piezoelectric cantilever sensor, wherein at least a portion of at least one target material potentially contained in the medium may still accumulate on the piezoelectric cantilever sensor without being removed;
- measuring a resonance frequency of the piezoelectric cantilever sensor; and
- comparing the measured resonance frequency with a baseline resonance frequency, wherein a difference between the measured resonance frequency and the baseline frequency is an indication that material has accumulated on the piezoelectric cantilever sensor.

27. A method in accordance with claim 26, the medium is not refined before exposing the at least one portion of the piezoelectric cantilever sensor to the medium.

28. A method in accordance with claim 26, further comprising
- applying mechanical energy to at least one of the medium or the piezoelectric cantilever sensor during exposure of the piezoelectric cantilever sensor to the medium, wherein application of the mechanical energy results in removal of at least one of:
  - a portion of target material accumulated on said piezoelectric cantilever sensor; or
  - a portion of non-target material accumulated on said piezoelectric cantilever sensor;
- measuring a resonance frequency of the piezoelectric cantilever sensor;
- comparing the measured resonance frequency with a baseline resonance frequency, wherein a difference between the measured resonance frequency and the baseline frequency is indicative that material was removed from the piezoelectric cantilever sensor.

29. A method in accordance with claim 26, wherein removal of at least a portion of non-target material accumulated on said piezoelectric cantilever sensor comprises removal of the at least a portion of non-target material that accumulated on the piezoelectric cantilever sensor during exposure to the medium.

30. A method in accordance with claim 26, wherein:
- during exposure of the at least a portion of the piezoelectric cantilever sensor to the medium; concurrently:
  - accumulating a portion of at least one target material that is contained in the medium; and
  - preventing accumulation on the piezoelectric cantilever sensor of at least a portion of at least one non-target material that is contained in the medium.

31. A method in accordance with claim 26, wherein:
- during exposure of the at least a portion of the piezoelectric cantilever sensor to the medium; concurrently:
  - accumulating at least a portion of at least one target material on the piezoelectric cantilever sensor that is contained in the medium; and
  - removing at least a portion of at least one non-target material that has accumulated on the piezoelectric cantilever sensor.

32. A method in accordance with claim 26, wherein the medium is a first medium, the method further comprising exposing the piezoelectric cantilever sensor to a second medium subsequent to applying mechanical energy to at least one of the first medium or the piezoelectric cantilever sensor.

* * * * *